(12) United States Patent
Zhao et al.

(10) Patent No.: US 12,605,381 B2
(45) **Date of Patent: *Apr. 21, 2026**

(54) METHOD FOR TREATING ENDOMETRIOSIS-ASSOCIATED PAIN BY USING DIAMINOPYRIMIDINE COMPOUND

(71) Applicant: BEIJING TIDE PHARMACEUTICAL CO., LTD., Beijing (CN)

(72) Inventors: Yanping Zhao, Beijing (CN); Huai Huang, Beijing (CN); Hongjun Wang, Beijing (CN); Yuanyuan Jiang, Beijing (CN); Huining Liang, Beijing (CN); Ran An, Beijing (CN); Zhou Lan, Beijing (CN); Jin Wang, Beijing (CN); Liying Zhou, Beijing (CN); Yanan Liu, Beijing (CN)

(73) Assignee: BEIJING TIDE PHARMACEUTICAL CO., LTD., Beijing (CN)

( * ) Notice: Subject to any disclaimer, the term of this patent is extended or adjusted under 35 U.S.C. 154(b) by 1109 days.

This patent is subject to a terminal disclaimer.

(21) Appl. No.: 17/607,475

(22) PCT Filed: Apr. 29, 2020

(86) PCT No.: PCT/CN2020/087689
§ 371 (c)(1),
(2) Date: Oct. 29, 2021

(87) PCT Pub. No.: WO2020/221277
PCT Pub. Date: Nov. 5, 2020

(65) Prior Publication Data

US 2022/0249478 A1 Aug. 11, 2022

(30) Foreign Application Priority Data

Apr. 30, 2019 (WO) ................ PCT/CN2019/085209

(51) Int. Cl.
*A61K 31/506* (2006.01)

(52) U.S. Cl.
CPC ................................. *A61K 31/506* (2013.01)

(58) Field of Classification Search
None
See application file for complete search history.

(56) References Cited

U.S. PATENT DOCUMENTS

| | | | | |
|---|---|---|---|---|
| 10,822,311 | B2 | 11/2020 | Hawley et al. | |
| 11,414,444 | B2 * | 8/2022 | Zhao | A61P 13/10 |
| 11,919,918 | B2 * | 3/2024 | Zhao | C07D 413/14 |

FOREIGN PATENT DOCUMENTS

| | | |
|---|---|---|
| CA | 3076680 | 5/2019 |
| CN | 108779119 | 11/2018 |
| CN | 108834412 | 11/2018 |
| JP | 2019-508445 | 3/2019 |
| JP | 2019-510025 | 4/2019 |
| JP | 2021-501184 | 1/2021 |
| MX | MX/a/2018/011136 | 1/2019 |
| WO | 2008104474 | 9/2008 |
| WO | 2019085916 | 5/2019 |

OTHER PUBLICATIONS

Ding et al. "P2X3 Receptor Involvement in Endometriosis Pain via ERK Signaling Pathway". PLoS ONE. 2017. 12(9):e0184647. (Year: 2017).*

Carter et al. "Identification and SAR of novel diaminopyrimidines. Part 1: the discovery of RO-4, a dual P2X3/P2X2/3 antagonist for the treatment of pain." Bioorganic & medicinal chemistry letters. Mar. 15, 2009;19(6):1628-31.

Shaojie Ding et al: "P2X3 receptor involvement in endometriosis pain via ERK signaling pathway", PLOS ONE, vol. 12, No. 9, Sep. 12, 2017, pp. 1-17, XP055735113.

G. Burnstock: "Purinergic mechanisms and pain—An update", European Journal of Pharmacology, vol. 716, No. 1, Mar. 22, 2013, pp. 24-40, XP028739261.

Komis et al. "2,4-Diamino-5-(pyridylmethyl)-pyrimidine als potentielle Chemotherapeutica", Eur. J. Med. Chem.—Chemica Therapeutica, 1977, 12(6), 531-536.

* cited by examiner

*Primary Examiner* — Leslie A. Royds Draper
(74) *Attorney, Agent, or Firm* — Robin L. Teskin; Baker, Donelson, Bearman, Caldwell & Berkowitz PC

(57) ABSTRACT

A method for treating, resisting and alleviating endometriosis-associated pain, relating to the field of biological medicine, comprising administering, to an individual in need thereof, a therapeutically effective amount of a diaminopyrimidine compound of formula (I) or a pharmaceutically acceptable salt, an ester, a stereoisomer, a polymorph, a solvate, an N-oxide, an isotopically labeled compound, a metabolite or a prodrug thereof.

Formula (I)

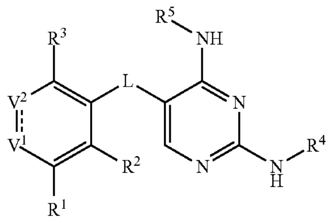

15 Claims, 5 Drawing Sheets

METHOD FOR TREATING ENDOMETRIOSIS-ASSOCIATED PAIN BY USING DIAMINOPYRIMIDINE COMPOUND

CROSS-REFERENCE TO RELATED APPLICATIONS

This application is a U.S. National Phase application of Int'l Appl. No. PCT/CN2020/087689, filed Apr. 29, 2020, which claims priority to Int'l Appl. No. PCT/CN2019/085209, filed Apr. 30, 2019, each of which are incorporated herein by reference in their entireties.

FIELD OF THE INVENTION

The present invention belongs to the field of biomedicine, and specifically relates to a method for treating, suppressing or alleviating endometriosis-associated pain, comprising administering to a subject in need thereof a therapeutically effective amount of a diaminopyrimidine compound or a pharmaceutically acceptable salt, ester, stereoisomer, polymorph, solvate, N-oxide, isotope-labeled compound, metabolite or prodrug thereof.

BACKGROUND OF THE INVENTION

Endometriosis is characterized by the presence of endometrioid tissue outside the uterine cavity, most frequently in the peritoneal cavity. Endometriosis almost exclusively affects premenopausal women, and is a highly prevalent and highly underdiagnosed condition. Endometriosis is a major cause of chronic pelvic pain, dyspareunia, and sub-fertility. This disease is usually found in women between the ages of 15 and 50.

When analgesics (e.g., cyclooxygenase-2 inhibitors) are ineffective, treatments for endometriosis currently aim at reducing or suppressing menstruation and estrogen production via the ovary. This is achieved by danazol, progesterone, oral contraceptive pills, or GnRH agonists. There are, however, many side effects. For example, the use of GnRH agonists is limited to 6 months because of their potential adverse effects on bone mineral density, and the treatment with danazol is also limited due to its side effect of androgen production. In addition, among patients who are responsive to the treatment with GnRH agonists, recurrence of the disease is reported in a majority of the patients within 5 years of treatment cessation.

The endometriosis-associated pain is the most difficult symptom to cope with for most women. For many women, the pain they suffer severely interferes with everyday life. It can be constant, or it can be cyclical and coincide with a woman's period.

SUMMARY OF THE INVENTION

In one aspect, the present invention provides a method for treating, suppressing or alleviating endometriosis-associated pain, comprising administering to a subject in need thereof a therapeutically effective amount of a compound of Formula (I) or a pharmaceutically acceptable salt, ester, stereoisomer, polymorph, solvate, N-oxide, isotopically labeled compound, metabolite or prodrug thereof:

Formula (I)

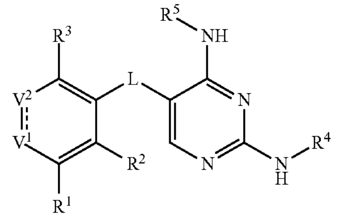

wherein:

L is selected from the group consisting of C(=O), CRR', NR, O, S, S=O and $S(=O)_2$;

$V^1$ is selected from the group consisting of N,

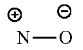

and NR;

$V^2$ is selected from the group consisting of $CR^6$ and C(=O);

⎓ represents either a single bond or a double bond, provided that when ⎓ is a single bond, $V^1$ is NR and $V^2$ is C(=O);

R and R' are each independently selected from the group consisting of H, halogen, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl, and at most 2 ring members in the cyclic hydrocarbyl and heterocyclyl are C(=O);

$R^1$, $R^2$, $R^3$ and $R^6$ are each independently selected from the group consisting of H, halogen, —CN, $—NO_2$, $—NH_2$, —OH, —SH, —Se—R, $—Si(R)_3$, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl, $C_{6-12}$ aralkyl, $C_{1-6}$ haloalkyl, $—C(=O)R^a$, $—OC(=O)R^a$, $—C(=O)OR^a$, $—OR^a$, $—SR^a$, $—S(=O)R^a$, $—S(=O)_2R^a$, $—S(=O)_2NR^aR^b$, $—S(=O)(=NR)R^a$, $—NR^aR^b$, $—C(=O)NR^aR^b$, $—C(=S)NR^aR^b$, $—C(=NR)NR^aR^b$, $—NR^a—C(=O)R^b$, $—NR^a—C(=O)OR^b$, $—NR^a—S(=O)_2—R^b$, $—NR^a—C(=O)—NR^aR^b$, $—C_{1-6}$ alkylene-$NR^aR^b$, $—C_{1-6}$ alkylene-$OR^a$, $—C_{1-6}$ alkylene-C(=O)R, $—C_{1-6}$ alkenylene-$OR^a$, $—O—C_{1-6}$ alkylene-$NR^aR^b$ and $—P(=O)R^aR^b$;

$R^4$ and $R^5$ are each independently selected from the group consisting of H, $—C(=O)OR^a$, $—NR^aR^b$, $—NR^a—C(=O)R^b$, $—NR^a—C(=O)OR^b$, $—C_{1-6}$ alkylene-$NR^aR^b$, $—C_{1-6}$ alkylene-$OR^a$, $—C_{1-6}$ alkylene-O—$C_{1-6}$ alkylene-$OR^a$, $C_{1-6}$ alkyl, $C_{1-6}$ haloalkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl;

alternatively, $R^1$ and $R^4$ together form —NH—($C_{1-6}$ alkylene)-L-($C_{1-6}$ alkylene)-, preferably $—NHCH_2CH_2—O—CH_2CH_2—$;

the above alkyl, alkylene, alkenyl, alkynyl, cyclic hydrocarbyl, heterocyclyl, aryl, heteroaryl and aralkyl, at each occurrence, are each optionally substituted with one or more substituents independently selected from the group consisting of halogen, hydroxyl, oxo, amino, cyano, nitro, —$Si(R)_3$, $C_{1-6}$ alkyl, saturated or partially unsaturated $C_{3-6}$ cyclic hydrocarbyl, saturated or partially unsaturated 3- to 10-membered heterocyclyl, $C_{6-10}$ aryl, 5- to 14-membered heteroaryl, $C_{6-12}$ aralkyl, —C(═O)$R^a$, —OC(═O)$R^a$, —C(═O)O$R^a$, —O$R^a$, —S$R^a$, —S(═O)$R^a$, —$S(═O)_2R^a$, —$S(═O)_2NR^aR^b$, —$NR^aR^b$, —C(═O)$NR^aR^b$, —$NR^a$—C(═O)$R^b$, —$NR^a$—C(═O)O$R^b$, —$NR^a$—$S(═O)_2$—$R^b$, —$NR^a$—C(═O)—$NR^aR^b$, —$C_{1-6}$ alkylene-$NR^aR^b$, —$C_{1-6}$ alkylene-O$R^a$, —$C_{1-6}$ alkenylene-O$R^a$ and —O—$C_{1-6}$ alkylene-$NR^aR^b$, the alkyl, cyclic hydrocarbyl, heterocyclyl, aryl, heteroaryl and aralkyl are further optionally substituted with one or more substituents independently selected from the group consisting of halogen, hydroxyl, oxo, amino, cyano, nitro, —$NR^aR^b$, $C_{1-6}$ alkyl, —O—$C_{1-6}$ alkyl, saturated or partially unsaturated $C_{3-6}$ cyclic hydrocarbyl, saturated or partially unsaturated 3- to 10-membered heterocyclyl, $C_{6-10}$ aryl, 5- to 14-membered heteroaryl and $C_{6-12}$ aralkyl; and $R^a$ and $R^b$, at each occurrence, are each independently selected from the group consisting of H, —OH, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl; alternatively, $R^a$ and $R^b$ together with the atom to which they are attached form a 3- to 12-membered heterocycle or heteroaromatic ring, the above groups are further optionally substituted with one or more substituents independently selected from the group consisting of halogen, hydroxyl, oxo, amino, cyano, nitro, $C_{1-6}$ alkyl, —O—$C_{1-6}$ alkyl, saturated or partially unsaturated $C_{3-6}$ cyclic hydrocarbyl, saturated or partially unsaturated 3- to 10-membered heterocyclyl, $C_{6-10}$ aryl, 5- to 14-membered heteroaryl and $C_{6-12}$ aralkyl.

In another aspect, the present invention provides use of a compound of above Formula (I) or a pharmaceutically acceptable salt, ester, stereoisomer, polymorph, solvate, N-oxide, isotopically labeled compound, metabolite or prodrug thereof in the manufacture of a medicament for treating, suppressing or alleviating endometriosis-associated pain.

In another aspect, the present invention provides a compound of above Formula (I) or a pharmaceutically acceptable salt, ester, stereoisomer, polymorph, solvate, N-oxide, isotopically labeled compound, metabolite or prodrug thereof for use of treating, suppressing or alleviating endometriosis-associated pain.

DETAILED DESCRIPTION OF THE INVENTION

Definition

Figure 1:
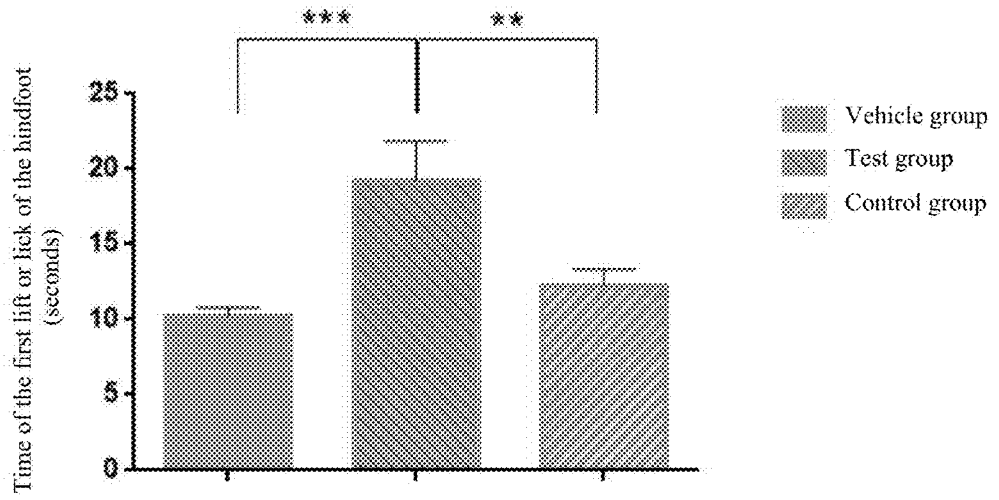
FIG. 1 shows the pain thresholds tested in endometriosis model rats in Example 1.

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

As used herein, the term "alkylene" refers to a saturated divalent hydrocarbyl, preferably refers to a saturated divalent hydrocarbyl having 1, 2, 3, 4, 5 or 6 carbon atoms, e.g., methylene, ethylene, propylene or butylene.

As used herein, the term "alkyl" is defined as a linear or branched saturated aliphatic hydrocarbon. In some embodiments, alkyl has 1-12, e.g., 1-6, carbon atoms. For example, as used herein, the term "$C_{1-6}$ alkyl" refers to a linear or branched group having 1-6 carbon atoms (such as methyl, ethyl, n-propyl, isopropyl, n-butyl, isobutyl, sec-butyl, tert-butyl, n-pentyl, isopentyl, neopentyl, or n-hexyl), which is optionally substituted with one or more (e.g., 1 to 3) suitable substituents such as halogen (in which case the group may be referred to as "haloalkyl") (e.g., $CH_2F$, $CHF_2$, $CF_3$, $CCl_3$, $C_2F_5$, $C_2Cl_5$, $CH_2CF_3$, $CH_2Cl$ or —$CH_2CH_2CF_3$ etc.). The term "$C_{1-4}$ alkyl" refers to a linear or branched aliphatic hydrocarbon chain having 1-4 carbon atoms (i.e., methyl, ethyl, n-propyl, isopropyl, n-butyl, isobutyl, sec-butyl or tert-butyl).

As used herein, the term "alkenyl" refers to a linear or branched monovalent hydrocarbyl having a double bond and 2-6 carbon atoms ("$C_{2-6}$ alkenyl"). The alkenyl is e.g., vinyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl and 4-methyl-3-pentenyl. When the compound of the present invention contains an alkenyl group, the compound may exist as the pure E (entgegen) form, the pure Z (zusammen) form, or any mixture thereof.

As used herein, the term "alkynyl" refers to a monovalent hydrocarbyl containing one or more triple bond, and preferably having 2, 3, 4, 5 or 6 carbon atoms, e.g., ethynyl or propynyl.

As used herein, the term "cycloalkyl" refers to a saturated monocyclic or polycyclic (e.g., bicyclic) hydrocarbon ring (e.g., monocyclic, such as cyclopropyl, cyclobutyl, cyclopentyl, cyclohexyl, cycloheptyl, cyclooctyl, or cyclononyl, or bicyclic, including spiro, fused or bridged cyclic system (such as bicyclo[1.1.1]pentyl, bicyclo[2.2.1]heptyl, bicyclo[3.2.1]octyl or bicyclo[5.2.0]nonyl, or decahydronaphthalene etc.)), which is optionally substituted with one or more (e.g., 1 to 3) suitable substituents. The cycloalkyl has 3 to 15 carbon atoms. For example, the term "$C_{3-6}$ cycloalkyl" refers to a saturated monocyclic or polycyclic (e.g., bicyclic) hydrocarbon ring having 3 to 6 ring forming carbon atoms (e.g., cyclopropyl, cyclobutyl, cyclopentyl, or cyclohexyl), which is optionally substituted with one or more (e.g., 1 to 3) suitable substituents, e.g., methyl substituted cyclopropyl.

As used herein, the terms "cyclic hydrocarbylene", "cyclic hydrocarbyl" and "hydrocarbon ring" refer to a saturated (i.e., "cycloalkylene" and "cycloalkyl") or unsaturated (i.e., having one or more double and/or triple bonds in the ring) monocyclic or polycyclic hydrocarbon ring having e.g., 3-10 (suitably having 3-8, and more suitably having 3-6) ring carbon atoms, including but not limited to cyclopropyl(ene) (ring), cyclobutyl(ene) (ring), cyclopentyl(ene) (ring), cyclohexyl(ene) (ring), cycloheptyl(ene) (ring), cyclooctyl(ene) (ring), cyclononyl(ene) (ring), cyclohexenyl (ene) (ring), and the like.

As used herein, the terms "heterocyclyl", "heterocyclylene" and "heterocycle" refer to a saturated (i.e., heterocycloalkyl) or partially unsaturated (i.e., having one or more double and/or triple bonds in the ring) cyclic group having e.g., 3-10 (suitably having 3-8, and more suitably having 3-6) ring atoms, wherein at least one ring atom is a heteroatom selected from the group consisting of N, O and S, and the remaining ring atoms are C. For example, "3- to 10-membered heterocyclyl(ene)" of "3- to 10-membered heterocycle" refers to saturated or partially unsaturated heterocyclyl(ene) or heterocycle having 2-9 (e.g., 2, 3, 4, 5, 6, 7, 8 or 9) ring carbon atoms and one or more (e.g., 1, 2, 3, or 4) heteroatoms independently selected from the group consisting of N, O and S. Examples of heterocyclylene, heterocyclyl and heterocycle include, but are not limited to oxiranyl(ene), aziridinyl(ene), azetidinyl(ene), oxetanyl (ene), tetrahydrofuranyl(ene), dioxolinyl(ene), pyrrolidinyl (ene), pyrrolidonyl(ene), imidazolidinyl(ene), pyrazolidinyl (ene), pyrrolinyl(ene), tetrahydropyranyl(ene), piperidinyl (ene), morpholinyl(ene), dithianyl(ene), thiomorpholinyl (ene), piperazinyl(ene) or trithianyl(ene). Said group also encompasses a bicyclic system, including a spiro, fused, or bridged system (e.g., 8-azaspiro[4.5]decane, 3,9-diazaspiro [5.5]undecane, 2-azabicyclo[2.2.2]octane, etc.). Heterocyclylene, heterocyclyl and heterocycle may optionally be substituted with one or more (e.g., 1, 2, 3 or 4) suitable substituents.

As used herein, the terms "aryl(ene)" and "aromatic ring" refer to an all-carbon monocyclic or fused-ring polycyclic aromatic group having a conjugated π electron system. For example, as used herein, the terms "$C_{6-10}$ aryl(ene)" and "$C_{6-10}$ aromatic ring" refer to an aromatic group containing 6 to 10 carbon atoms, such as phenyl(ene) (benzene ring) or naphthyl(ene) (naphthalene ring). Aryl(ene) or aromatic ring is optionally substituted with one or more (such as 1 to 3) suitable substituents (e.g., halogen, —OH, —CN, —$NO_2$, and $C_{1-6}$ alkyl, etc.).

As used herein, the terms "heteroaryl(ene)" and "heteroaromatic ring" refer to a monocyclic, bicyclic or tricyclic aromatic ring system having 5, 6, 8, 9, 10, 11, 12, 13 or 14 ring atoms, particularly 1 or 2 or 3 or 4 or 5 or 6 or 9 or 10 carbon atoms, and containing at least one heteroatom (such as O, N, or S), which can be same to different. Moreover, in each case, it can be benzo-fused. In particular, "heteroaryl (ene)" or "heteroaromatic ring" is selected from the group consisting of thienyl(ene), furyl(ene), pyrrolyl(ene), oxazolyl(ene), thiazolyl(ene), imidazolyl(ene), pyrazolyl(ene), isoxazolyl(ene), isothiazolyl(ene), oxadiazolyl(ene), triazolyl(ene), thiadiazolyl(ene) etc., and benzo derivatives thereof; or pyridinyl(ene), pyridazinyl(ene), pyrimidinyl (ene), pyrazinyl(ene), triazinyl(ene), etc., and benzo derivatives thereof.

As used herein, the term "aralkyl" preferably means aryl or heteroaryl substituted alkyl, wherein aryl, heteroaryl and alkyl are as defined herein. Normally, the aryl group may have 6-14 carbon atoms, the heteroaryl group may have 5-14 ring atoms, and the alkyl group may have 1-6 carbon atoms. Exemplary aralkyl group includes, but is not limited to, benzyl, phenylethyl, phenylpropyl, phenylbutyl.

As used herein, the term "halo" or "halogen" are defined to include F, Cl, Br, or I.

As used herein, the term "nitrogen containing heterocycle" refers to a saturated or unsaturated monocyclic or bicyclic group having 2, 3, 4, 5, 6, 7, 8, 9, 10, 11, 12 or 13 carbon atoms and at least one nitrogen atom in the ring, which may further optionally comprise one or more (e.g., one, two, three or four) ring members selected from the group consisting of N, O, C═O, S, S═O and S(═O)$_2$. The nitrogen containing heterocycle is attached to the rest of the molecule through the nitrogen atom and any other ring atom in said nitrogen containing heterocycle. The nitrogen containing heterocycle is optionally benzo-fused, and is preferably attached to the rest of the molecule through the nitrogen atom in said nitrogen containing heterocycle and any carbon atom in the fused benzene ring.

The term "substituted" means that one or more (e.g., one, two, three, or four) hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

If a substituent is described as being "optionally substituted", the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more from a list of substituents, one or more of the hydrogens on the nitrogen (to the extent there are any) may each be replaced with an independently selected optional substituent.

If substituents are described as being "independently selected" from a group, each substituent is selected independent of the other(s). Each substituent therefore may be identical to or different from the other substituent(s).

As used herein, the term "one or more" means one or more than one (e.g., 2, 3, 4, 5 or 10) as reasonable.

As used herein, unless specified, the point of attachment of a substituent can be from any suitable position of the substituent.

When a bond to a substituent is shown to cross a bond connecting two atoms in a ring, then such substituent may be bonded to any of the ring-forming atoms in that ring that are substitutable.

The present invention also includes all pharmaceutically acceptable isotopically labeled compounds, which are identical to those of the present invention except that one or more atoms are replaced by an atom having the same atomic number, but an atomic mass or mass number different from the atomic mass or mass number which predominates in nature. Examples of isotopes suitable for inclusion in the compound of the present invention include, but are not limited to, isotopes of hydrogen, such as $^{2}H$, $^{3}H$; carbon, such as $^{11}C$, $^{13}C$, and $^{14}C$; chlorine, such as $^{36}Cl$; fluorine, such as $^{18}F$; iodine, such as $^{123}I$ and $^{125}I$; nitrogen, such as $^{13}N$ and $^{15}N$; oxygen, such as $^{15}O$, $^{17}O$, and $^{18}O$; phosphorus, such as $^{32}P$; and sulfur, such as $^{35}S$. Certain isotopically labeled compounds of the present invention, for example those incorporating a radioactive isotope, are useful in drug and/or substrate tissue distribution studies (e.g., assays). The radioactive isotopes tritium, i.e., $^{3}H$, and carbon-14, i.e., $^{14}C$, are particularly useful for this purpose in view of their ease of incorporation and ready means of detection. Substitution with positron-emitting isotopes, such as $^{11}C$, $^{18}F$, $^{15}O$ and $^{13}N$, can be useful in positron emission tomography (PET) studies for examining substrate receptor occupancy. Isotopically labeled compounds of the present invention can generally be prepared by processes analogous to those described in the accompanying Schemes and/or in the Examples and Preparations, by using an appropriate isotopically labeled reagent in place of the non-labeled reagent previously employed. Pharmaceutically acceptable solvates in accordance with the invention include those wherein the solvent of crystallization may be isotopically substituted, e.g., $D_2O$, acetone-$d_6$, or DMSO-$d_6$.

The term "stereoisomer" refers to isomers with at least one asymmetric center. A compound having one or more (e.g., one, two, three or four) asymmetric centers can give rise to a racemic mixture, single enantiomer, diastereomer mixture and individual diastereomer. Certain individual molecules may exist as geometric isomers (cis/trans). Similarly, the compound of the present invention may exist as a mixture of two or more structurally different forms in rapid equilibrium (generally referred to as tautomer). Typical examples of a tautomer include a keto-enol tautomer, phenol-keto tautomer, nitroso-oxime tautomer, imine-enamine tautomer and the like. It is to be understood that all such isomers and mixtures thereof in any proportion (such as 60%, 65%, 70%, 75%, 80%, 85%, 90%, 95%, 96%, 97%, 98%, and 99%) are encompassed within the scope of the present invention.

The chemical bonds of the compound of the present invention may be depicted herein using a solid line (—), a solid wedge (▬), or a dotted wedge (┅). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Unless stated otherwise, it is intended that the compound of the present invention can exist as stereoisomers, which include cis and trans isomers, optical isomers such as R and S enantiomers, diastereomers, geometric isomers, rotational isomers, conformational isomers, atropisomers, and mixtures thereof. The compound of the present invention may exhibit more than one type of isomerism, and consist of mixtures thereof (such as racemates and diastereomeric pairs).

The present invention includes all possible crystalline forms or polymorphs of the compound of the present invention, either as a single polymorph, or as a mixture of more than one polymorphs, in any ratio.

It also should be understood that, certain compounds of the present invention can be used for the treatment in a free form, or where appropriate, in a form of a pharmaceutically acceptable derivative. In the present invention, the pharmaceutically acceptable derivative includes, but is not limited to a pharmaceutically acceptable salt, ester, solvate, N-oxide, metabolite or prodrug, which can directly or indirectly provide the compound of the present invention or a metabolite or residue thereof after being administered to a patient in need thereof. Therefore, "the compound of the present invention" mentioned herein also means to encompass various derivative forms of the compound as mentioned above.

A pharmaceutically acceptable salt of the compound of the present invention includes an acid addition salt and a base addition salt thereof.

A suitable acid addition salt is formed from an acid which forms a pharmaceutically acceptable salt. Specific examples include acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

A suitable base addition salt is formed from a base which forms a pharmaceutically acceptable salt. Specific examples include aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, 2002). The method for preparing a pharmaceutically acceptable salt of the compound of the present invention is known to a person skilled in the art.

As used herein, the term "ester" refers to those derived from the compounds of the various formulae in the present application, which include physiologically-hydrolyzable esters (which may be hydrolyzed under physiological conditions to release the compounds of the present invention in the form of free acids or alcohols). The compound of the present invention itself may be an ester as well.

The compound of the present invention can exist as a solvate (preferably a hydrate), wherein the compound of the present invention contains a polar solvent, in particular water, methanol or ethanol for example, as a structural element of the crystal lattice of the compound. The amount of the polar solvent, in particular water, may exist in a stoichiometric or non-stoichiometric ratio.

As can be appreciated by a person skilled in the art, not all nitrogen containing heterocycles can form N-oxides since the nitrogen requires an available lone-pair electron for oxidation to the oxide; a person skilled in the art will recognize those nitrogen containing heterocycles which can form N-oxides. A person skilled in the art will also recognize that tertiary amines can form N-oxides. Synthetic methods for the preparation of N-oxides of heterocycles and tertiary amines are well known to a person skilled in the art, and they include the oxidation of heterocycles and tertiary amines with peroxy acids such as peracetic acid and m-chloroperbenzoic acid (MCPBA), hydrogen peroxide, alkyl hydroperoxides such as tert-butyl hydroperoxide, sodium perborate, and dioxiranes such as dimethyldioxirane. These methods for the preparation of N-oxides have been extensively described and reviewed in literatures, see e.g., T. L. Gilchrist, *Comprehensive Organic Synthesis*, vol. 7, pp 748-750; A. R. Katritzky and A. J. Boulton, Eds., Academic Press; and G. W. H. Cheeseman and E. S. G. Werstiuk, *Advances in Heterocyclic Chemistry*, vol. 22, pp 390-392, A. R. Katritzky and A. J. Boulton, Eds., Academic Press.

The metabolite of the compound of the present invention, namely a substance formed in vivo upon administration of the compound of the present invention, is also included within the scope of the present invention. Such a product may result e.g., from the oxidation, reduction, hydrolysis, amidation, de-amidation, esterification, enzymolysis, and the like, of the administered compound. Accordingly, the present invention encompasses the metabolite of the compound of the present invention, including a compound produced by a method comprising contacting the compound of the present invention with a mammal for a period of time sufficient to result in a metabolic product thereof.

Also within the scope of the present invention is a prodrug of the compound of the invention, which is certain derivative of the compound of the invention that may have little or no pharmacological activity itself, but can, when administered into or onto the body, be converted into the compound of the invention having the desired activity, for example, by hydrolytic cleavage. In general, such prodrug will be a functional derivative of the compound which is readily converted in vivo into the compound with desired therapeutic activity. Further information on the use of the prodrug may be found in "Pro-drugs as Novel Delivery Systems", Vol. 14, ACS Symposium Series (T. Higuchi and V. Stella). The prodrug in accordance with the invention can, for example, be produced by replacing appropriate functionalities present in the compound of the present invention with certain moieties known to those skilled in the art as "pro-moieties" as described, for example, in "Design of Prodrugs" by H. Bundgaard (Elsevier, 1985).

The present invention further encompasses the compound of the present invention having a protecting group. During any of the processes for preparation of the compound of the present invention, it may be necessary and/or desirable to protect sensitive or reactive groups on any of the molecules concerned, thereby resulting in the chemically protected form of the compound of the present invention. This may be achieved by means of conventional protecting groups, e.g., those described in T. W. Greene & P. G. M. Wuts, Protective Groups in Organic Synthesis, John Wiley & Sons, 1991, which is incorporated herein by reference. The protecting groups may be removed at a convenient subsequent stage using methods known from the art.

The term "about" refers to a range within ±10%, preferably within ±5%, and more preferably within ±2% of the specified value.

As used herein, the term "effective amount" refers to the amount of a compound being administered which will relieve to some extent one or more of the symptoms of the disorder being treated.

Unless otherwise indicated, the term "treating" or "treatment", as used herein, means reversing, alleviating, inhibiting the progress of, or preventing the disorder or condition to which such term applies, or one or more symptoms of such disorder or condition.

As used herein, the term "subject" includes a human or non-human animal Δn exemplary human subject includes a human subject having a disease (such as one described herein) (referred to as a patient), or a normal subject. The term "non-human animal" as used herein includes all vertebrates, such as non-mammals (e.g., birds, amphibians, reptiles) and mammals, such as non-human primates, livestock and/or domesticated animals (such as sheep, dog, cat, cow, pig and the like).

MODE OF CARRYING OUT THE INVENTION

In some embodiments, the present invention provides a method for treating, suppressing or alleviating endometriosis-associated pain, comprising administering to a subject in need thereof a therapeutically effective amount of a compound of Formula (I) or a pharmaceutically acceptable salt, ester, stereoisomer, polymorph, solvate, N-oxide, isotopically labeled compound, metabolite or prodrug thereof:

Formula (I)

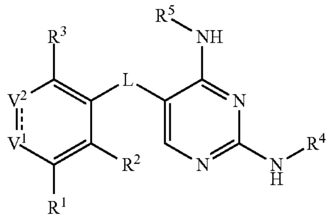

wherein:

L is selected from the group consisting of C(=O), CRR', NR, O, S, S=O and $S(=O)_2$;

$V^1$ is selected from the group consisting of N,

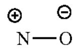

and NR;

$V^2$ is selected from the group consisting of $CR^6$ and C(=O);

⎓ represents either a single bond or a double bond, provided that when ⎓ is a single bond, $V^1$ is NR and $V^2$ is C(=O);

R and R' are each independently selected from the group consisting of H, halogen, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl, and at most 2 ring members in the cyclic hydrocarbyl and heterocyclyl are C(=O);

$R^1$, $R^2$, $R^3$ and $R^6$ are each independently selected from the group consisting of H, halogen, —CN, —$NO_2$, —$NH_2$, —OH, —SH, —Se—R, —$Si(R)_3$, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl, $C_{6-12}$ aralkyl, $C_{1-6}$ haloalkyl, —C(=O)$R^a$, —OC(=O)$R^a$, —C(=O)O$R^a$, —O$R^a$, —S$R^a$, —S(=O)$R^a$, —$S(=O)_2R^a$, —$S(=O)_2NR^aR^b$, —S(=O)(=NR)$R^a$, —$NR^aR^b$, —C(=O)$NR^aR^b$, —C(=S)$NR^aR^b$, —C(=NR)$NR^aR^b$, —$NR^a$—C(=O)$R^b$, —$NR^a$—C(=O)O$R^b$, —$NR^a$—$S(=O)_2$—$R^b$, —$NR^a$—C(=O)—$NR^aR^b$, —$C_{1-6}$ alkylene-$NR^aR^b$, —$C_{1-6}$ alkylene-O$R^a$, —$C_{1-6}$ alkylene-C(=O)R, —$C_{1-6}$ alkenylene-O$R^a$, —O—$C_{1-6}$ alkylene-$NR^aR^b$ and —P(=O)$R^aR^b$;

$R^4$ and $R^5$ are each independently selected from the group consisting of H, —C(=O)O$R^a$, —$NR^aR^b$, —$NR^a$—C(=O)$R^b$, —$NR^a$—C(=O)O$R^b$, —$C_{1-6}$ alkylene-$NR^aR^b$, —$C_{1-6}$ alkylene-O$R^a$, —$C_{1-6}$ alkylene-O—$C_{1-6}$ alkylene-O$R^a$, $C_{1-6}$ alkyl, $C_{1-6}$ haloalkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl;

alternatively, $R^1$ and $R^4$ together form —NH—($C_{1-6}$ alkylene)-L-($C_{1-6}$ alkylene)-, preferably —$NHCH_2CH_2$—O—$CH_2CH_2$—;

the above alkyl, alkylene, alkenyl, alkynyl, cyclic hydrocarbyl, heterocyclyl, aryl, heteroaryl and aralkyl, at each occurrence, are each optionally substituted with one or more substituents independently selected from the group consisting of halogen, hydroxyl, oxo, amino, cyano, nitro, —$Si(R)_3$, $C_{1-6}$ alkyl, saturated or partially unsaturated $C_{3-6}$ cyclic hydrocarbyl, saturated or partially unsaturated 3- to 10-membered heterocyclyl, $C_{6-10}$ aryl, 5- to 14-membered heteroaryl, $C_{6-12}$ aralkyl, —C(═O)$R^a$, —OC(═O)$R^a$, —C(═O)O$R^a$, —O$R^a$, —S$R^a$, —S(═O)$R^a$, —S(═O)$_2R^a$, —S(═O)$_2NR^aR^b$, —$NR^aR^b$, —C(═O)$NR^aR^b$, —$NR^a$—C(═O)$R^b$, —$NR^a$—C(═O)O$R^b$, —$NR^a$—S(═O)$_2$—$R^b$, —$NR^a$—C(═O)—$NR^aR^b$, —$C_{1-6}$ alkylene-$NR^aR^b$, —$C_{1-6}$ alkylene-O$R^a$, —$C_{1-6}$ alkenylene-O$R^a$ and —O—$C_{1-6}$ alkylene-$NR^aR^b$, the alkyl, cyclic hydrocarbyl, heterocyclyl, aryl, heteroaryl and aralkyl are further optionally substituted with one or more substituents independently selected from the group consisting of halogen, hydroxyl, oxo, amino, cyano, nitro, —$NR^aR^b$, $C_{1-6}$ alkyl, —O—$C_{1-6}$ alkyl, saturated or partially unsaturated $C_{3-6}$ cyclic hydrocarbyl, saturated or partially unsaturated 3- to 10-membered heterocyclyl, $C_{6-10}$ aryl, 5- to 14-membered heteroaryl and $C_{6-12}$ aralkyl; and $R^a$ and $R^b$, at each occurrence, are each independently selected from the group consisting of H, —OH, $C_{1-6}$ alkyl, $C_{2-6}$ alkenyl, $C_{2-6}$ alkynyl, saturated or partially unsaturated $C_{3-10}$ cyclic hydrocarbyl, saturated or partially unsaturated 3- to 10-membered heterocyclyl, $C_{6-10}$ aryl, 5- to 14-membered heteroaryl and $C_{6-12}$ aralkyl; alternatively, $R^a$ and $R^b$ together with the atom to which they are attached form a 3- to 12-membered heterocycle or heteroaromatic ring, the above groups are further optionally substituted with one or more substituents independently selected from the group consisting of halogen, hydroxyl, oxo, amino, cyano, nitro, $C_{1-6}$ alkyl, —O—$C_{1-6}$ alkyl, saturated or partially unsaturated $C_{3-6}$ cyclic hydrocarbyl, saturated or partially unsaturated 3- to 10-membered heterocyclyl, $C_{6-10}$ aryl, 5- to 14-membered heteroaryl and $C_{6-12}$ aralkyl.

In other embodiments, the present invention provides use of a compound of above Formula (I) or a pharmaceutically acceptable salt, ester, stereoisomer, polymorph, solvate, N-oxide, isotopically labeled compound, metabolite or prodrug thereof in the manufacture of a medicament for treating, suppressing or alleviating endometriosis-associated pain.

In other embodiments, the present invention provides a compound of above Formula (I) or a pharmaceutically acceptable salt, ester, stereoisomer, polymorph, solvate, N-oxide, isotopically labeled compound, metabolite or prodrug thereof for use of treating, suppressing or alleviating endometriosis-associated pain.

In preferred embodiments, L is selected from the group consisting of $CH_2$, O, S and NH.

In preferred embodiments, $V^1$ is selected from the group consisting of N, $$\overset{\oplus}{N}-\overset{\ominus}{O}$$

and $NCH_3$.

In preferred embodiments, $V^2$ is selected from the group consisting of CH, C—$NHCH_3$, C—$OCH_3$, C—F and C(═O).

In preferred embodiments, $R^a$ and $R^b$, at each occurrence, are each independently selected from the group consisting of H, —OH, methyl, ethyl, n-propyl, isopropyl, cyclopropyl, phenyl, benzyl, methoxy and ethoxy; alternatively, $R^a$ and $R^b$ together with the atom to which they are attached form a 5- to 8-membered heterocycle or heteroaromatic ring.

In preferred embodiments, $R^1$, $R^2$, $R^3$ and $R^6$ are each independently selected from the group consisting of H, F, Cl, Br, I, —CN, —$NH_2$, —OH, —SH, —Se—$CH_3$, —$Si(CH_3)_3$, —$CH_2NH_2$, —$CH_2NHCH_3$, —$CH_2N(CH_3)_2$, methyl, ethyl, n-propyl, isopropyl, n-butyl, isobutyl, tert-butyl, cyclopropyl, cyclobutyl, cyclopentyl, cyclohexyl, vinyl, propenyl, allyl, ethynyl, propynyl, trifluoromethyl, acetyl, —C(═O)OH, —C(═O)$NH_2$, —C(═S)$NH_2$, —C(═NH)$NH_2$, —$NHCH_3$, —$NHCH_2CH_3$, —$NHCH_2CF_3$, —$N(CH_3)_2$, —$N(CH_3)(C_2H_5)$, —$N(C_2H_5)_2$, —$NHCH_2CH_2OH$, —NH—C(═O)$CH_3$, —NH—C(═O)CH═$CH_2$, methoxy, ethoxy, propoxy, phenyl, —NH—C(═O)—$NH_2$, —NH—C(═O)$OCH_3$, —$SCH_3$, —$SCH_2CH_3$, —$SC(CH_3)_3$, —SBn, —S(═O)$CH_3$, —S(═O)Bn, —S(═O)$_2CH_3$, —S(═O)$_2$Bn, —S(═O)$_2NH_2$, —S(═O)$_2NHCH_3$, —S(═O)$_2N(CH_3)_2$, —S(═O)(═NH)$CH_3$, —P(═O)$(CH_3)_2$, —P(═O)$(C_2H_5)_2$,

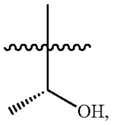,
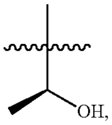,
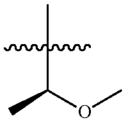,
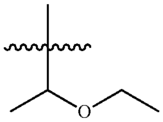,
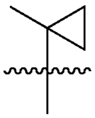,
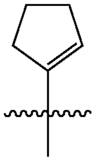,
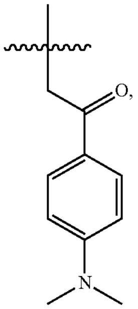,
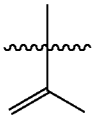,
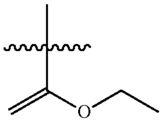,
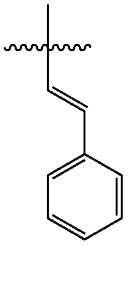,
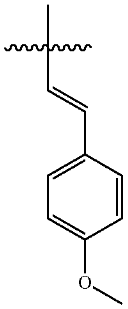,
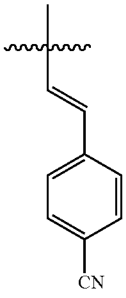, -continued
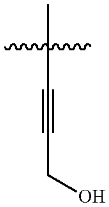,
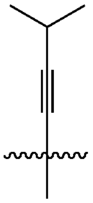,
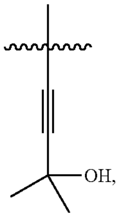
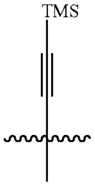,
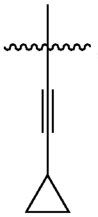,
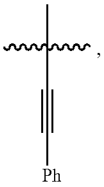,
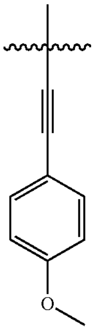,
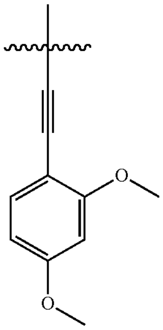,
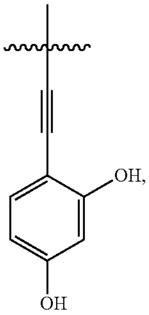
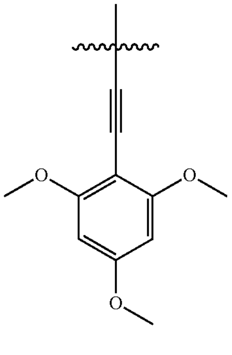,
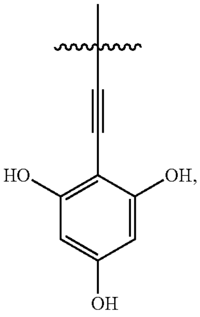
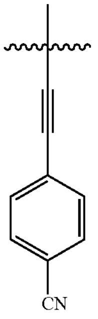,
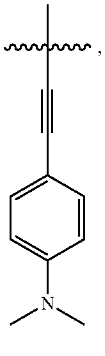,
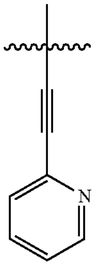,
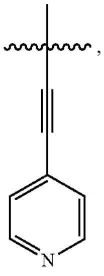,
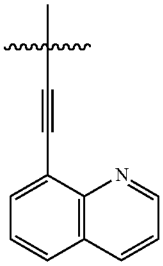,
-continued
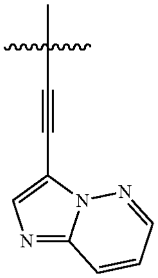,
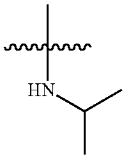,
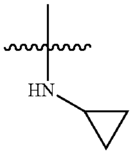,
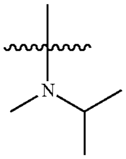,
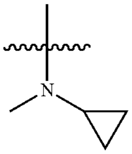,
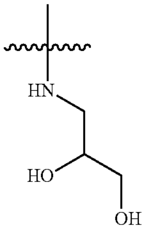,
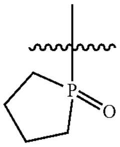,
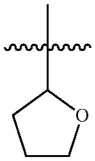,
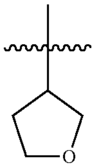,
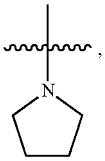,
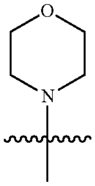,
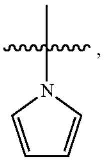,
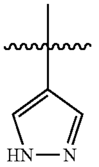,
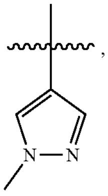,
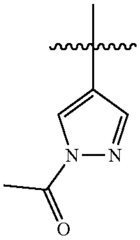,
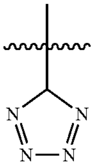,
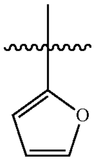,
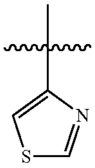,
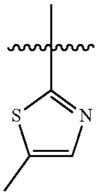 and
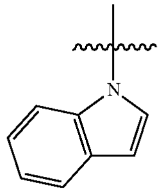.
In preferred embodiments, $R^4$ and $R^5$ are each independently selected from the group consisting of H, —C(=O)OC($CH_3$)$_3$, —$NH_2$, —$NHCH_3$, —NHPh, —NHC(=O)$CH_3$, —NHBoc, methyl, ethyl, —$CH_2CF_3$, n-propyl, isopropyl, n-butyl, isobutyl, tert-butyl, cyclopropyl, cyclobutyl, cyclopentyl, cyclohexyl, phenyl, benzyl,

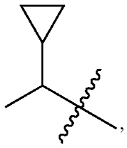, 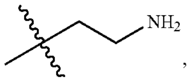, 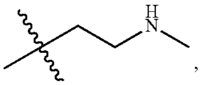,
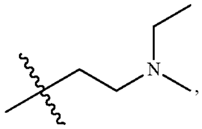, 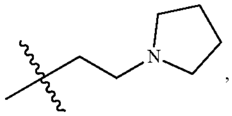,
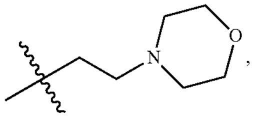, 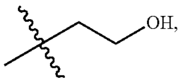
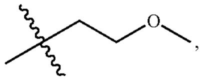, 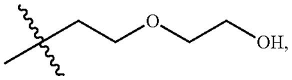
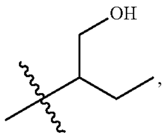, 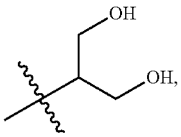
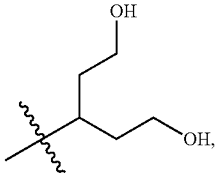 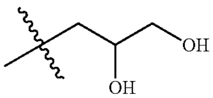 and
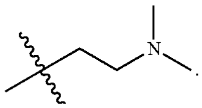.
In preferred embodiments, the compound of Formula (I) has the structure of any of the following formulae:
(II)
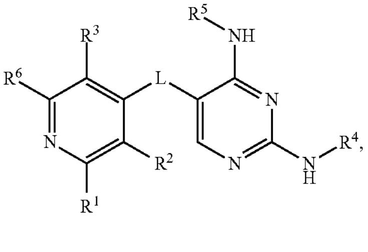
(III)
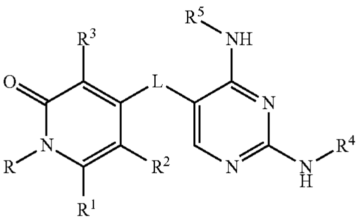 or
-continued
(IV)
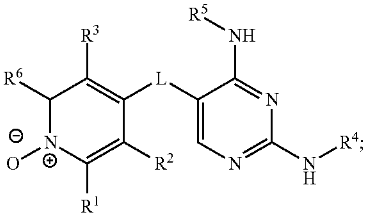
preferably has the structure of any of the following formulae:
(II′)
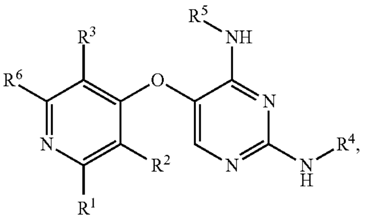
(III′)
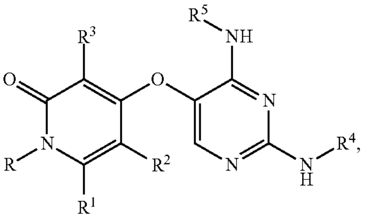
(IV′)
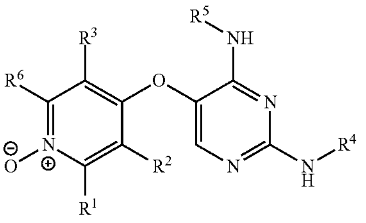
(II″)
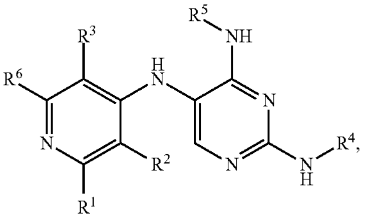
(III″)
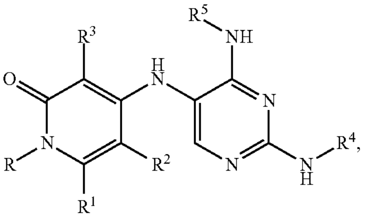

-continued (IV'')

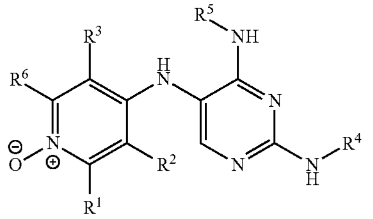

(II''')

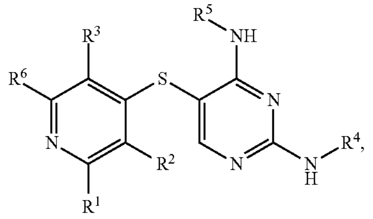

(III''')

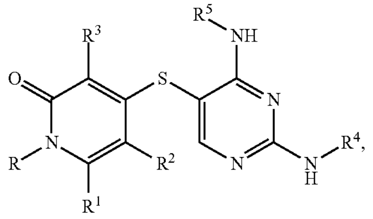

(IV''')

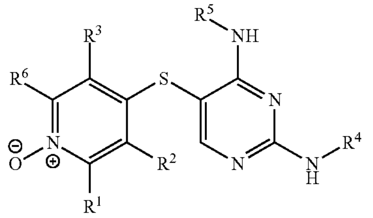

(II'''')

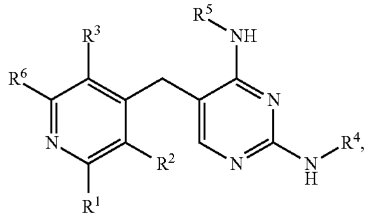

(III'''')

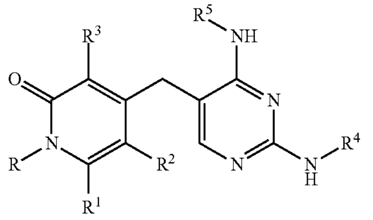

or (IV'''')

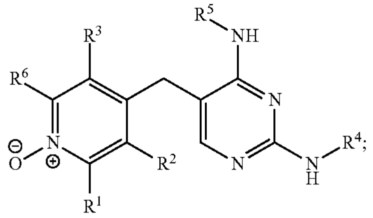

more preferably, the compound of Formula (I) has the structure of any of the following formulae:

(II'-1)

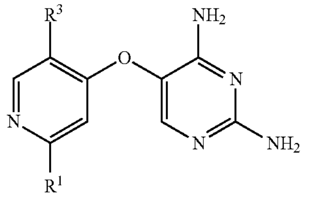

wherein:

$R^1$ is selected from the group consisting of F, Cl, Br, I and $C_{2-6}$ alkynyl, preferably Br or ethynyl; and $R^3$ is $C_{1-6}$ alkyl, preferably isopropyl.

The technical solution obtained by any combination of the various embodiments is encompassed by the invention.

In preferred embodiments, the compound of Formula (I) has the following structure:

1

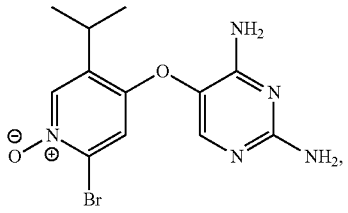

2

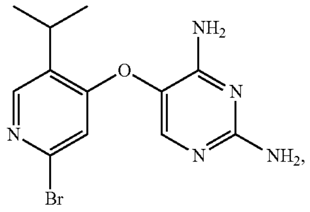

3

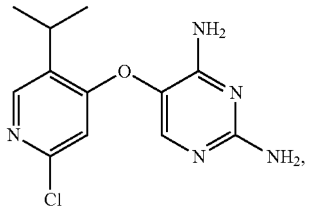

4

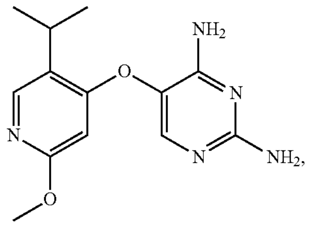

-continued
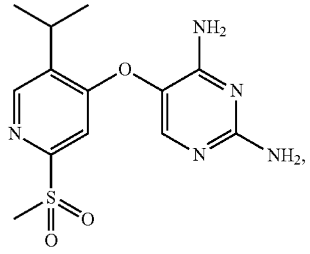
5
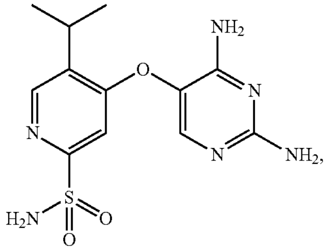
6
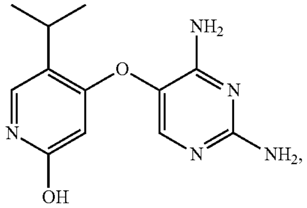
7
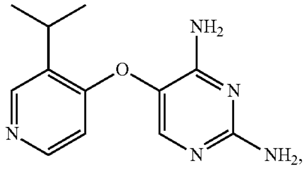
8
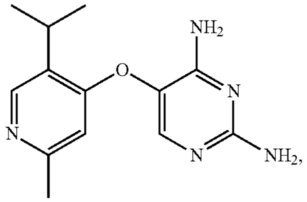
9
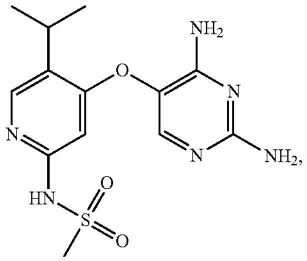
10
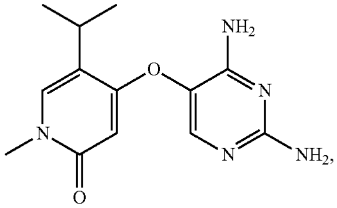
11
-continued
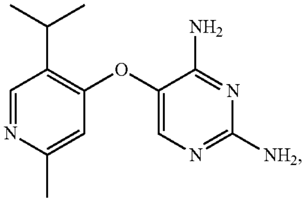
12
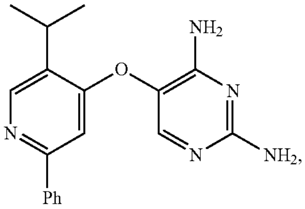
13
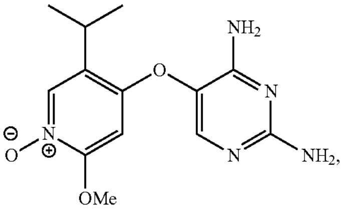
14
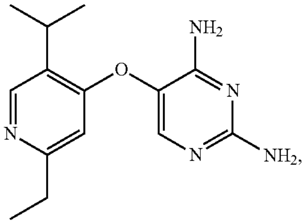
15
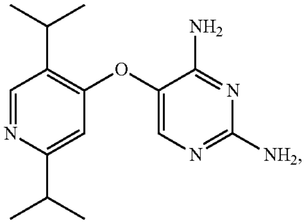
16
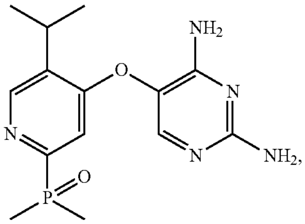
17
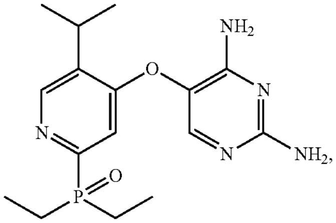
18

-continued
19
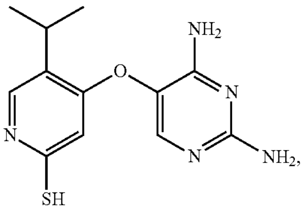
20
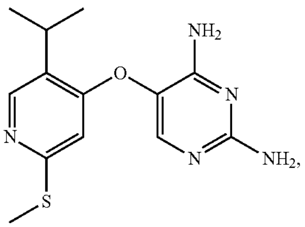
21
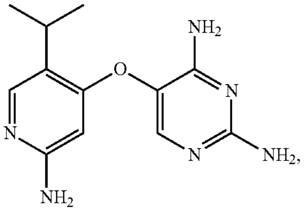
22
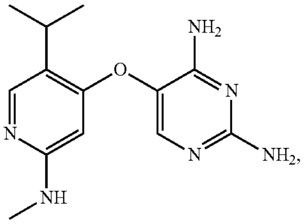
23
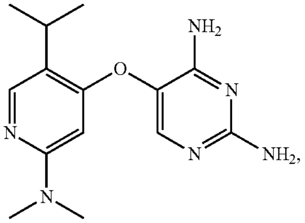
24
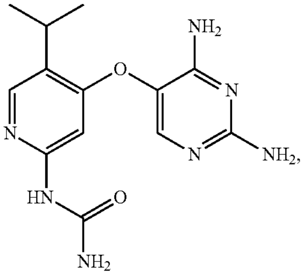
-continued
25
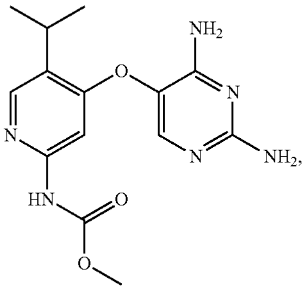
26
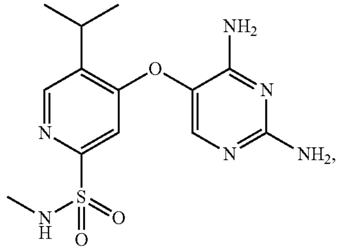
27
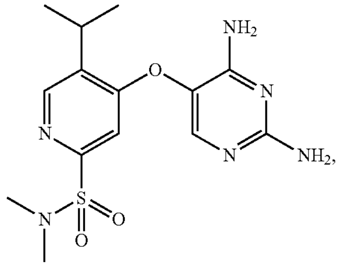
28
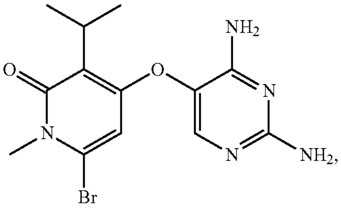
29
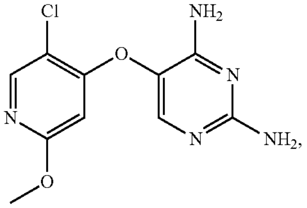
30
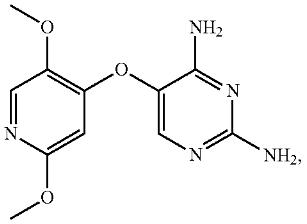

-continued
31
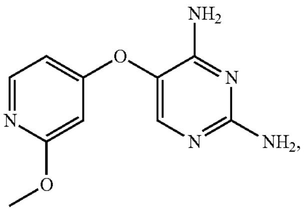
32
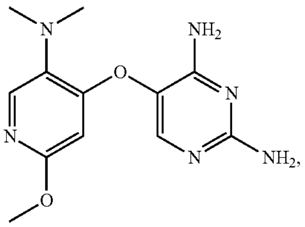
33
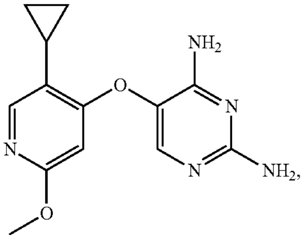
34
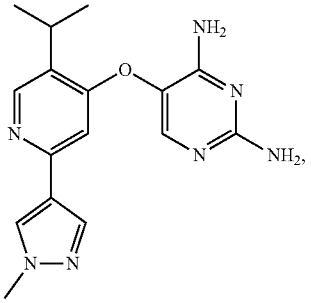
35
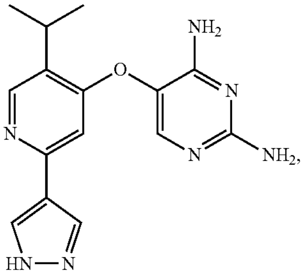
36
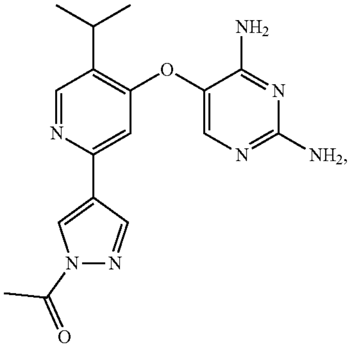
-continued
37
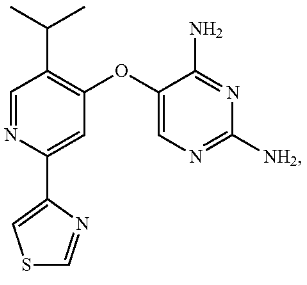
38
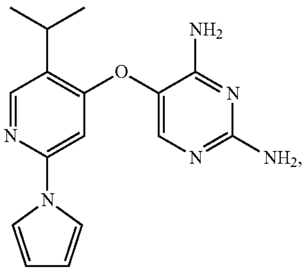
39
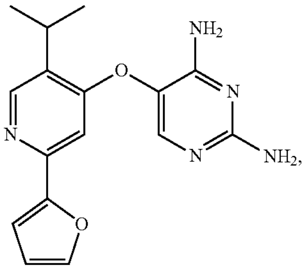
40
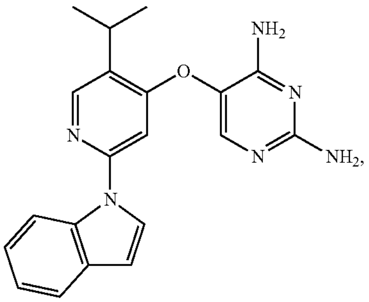
41
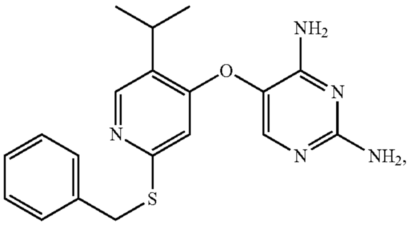

-continued
42
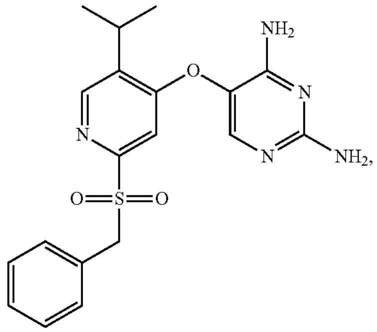
43
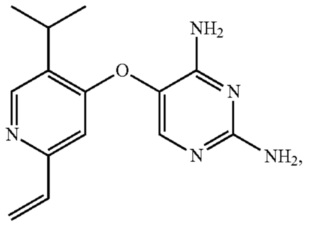
44
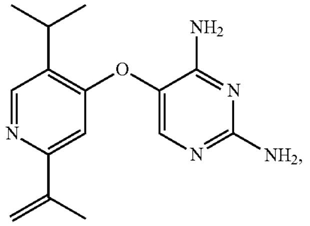
45
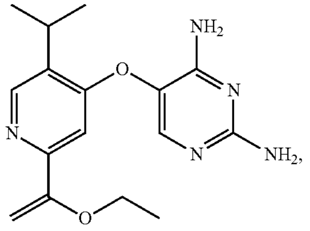
46
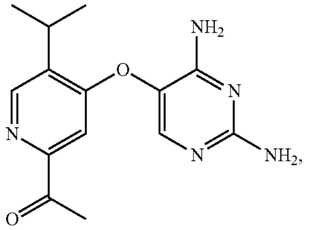
47
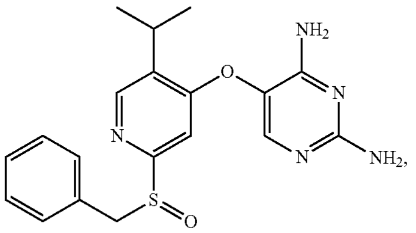
-continued
48
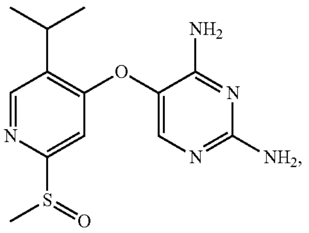
49
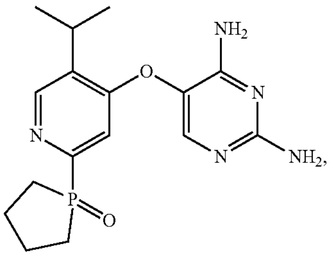
50
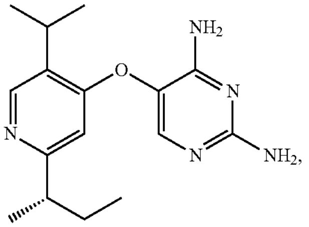
51
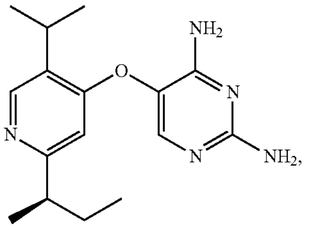
52
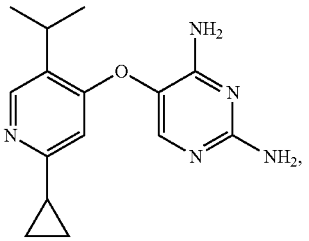
53
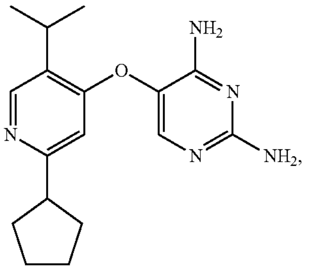

-continued
54
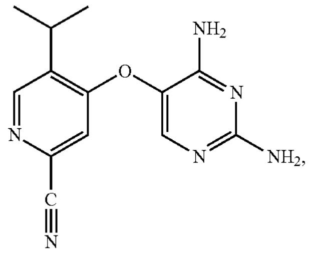
55
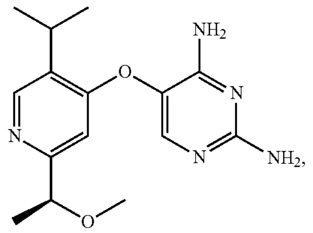
56
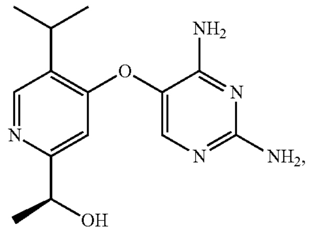
57
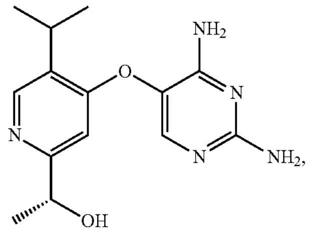
58
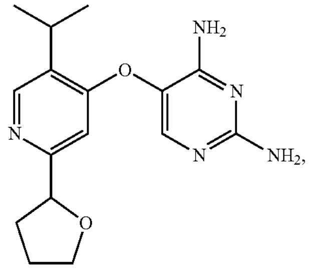
59
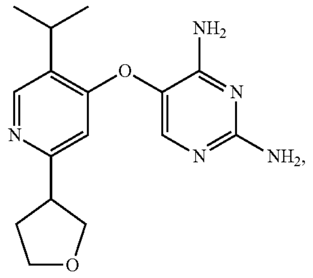
-continued
60
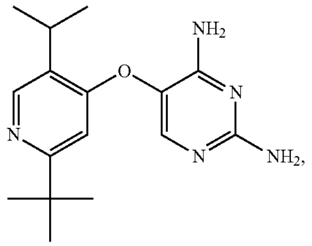
61
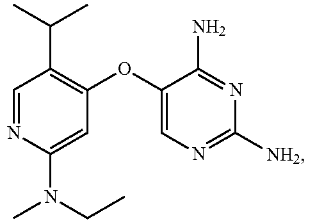
62
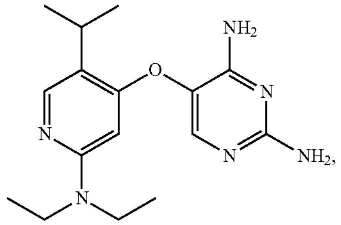
63
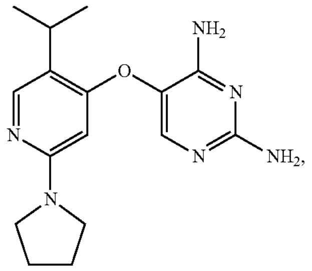
64
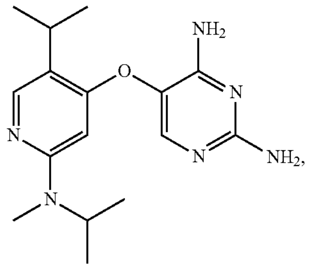
65
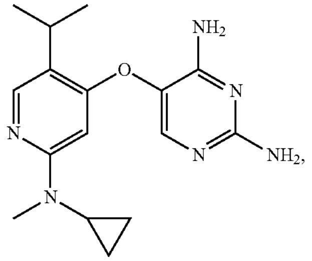

-continued
66
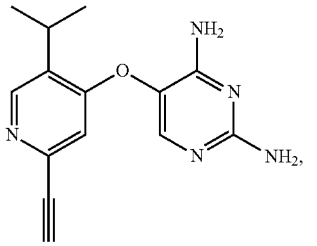
67
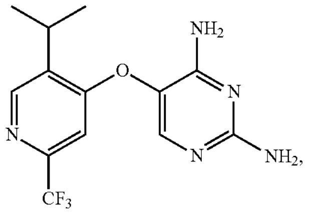
68
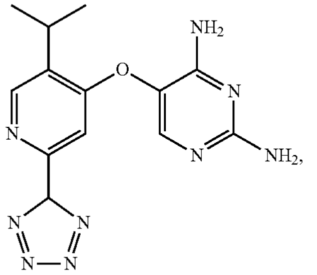
69
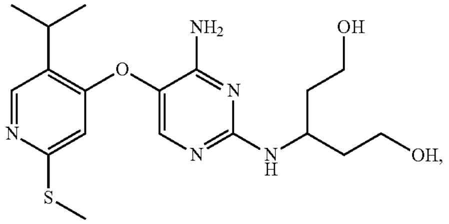
70
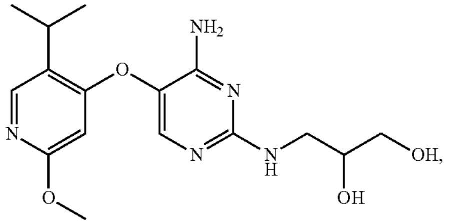
71
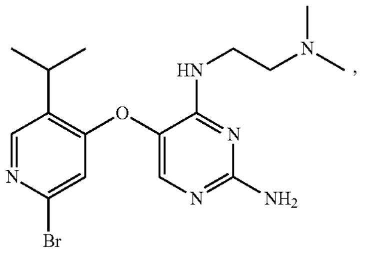
-continued
72
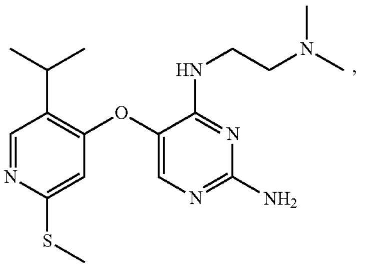
73
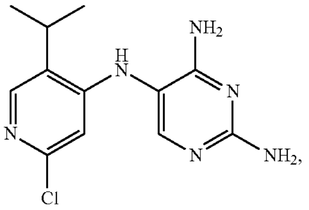
74
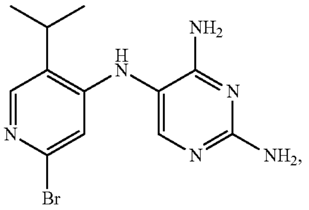
75
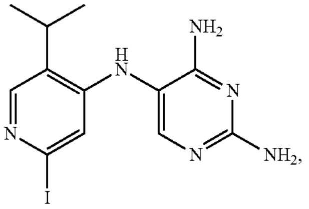
76
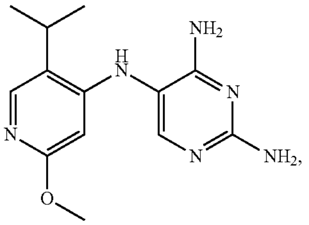
77
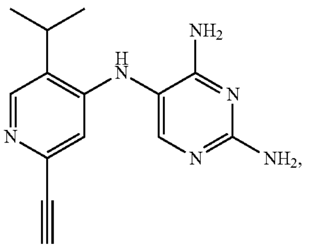

-continued
78
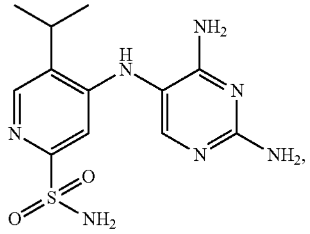
79
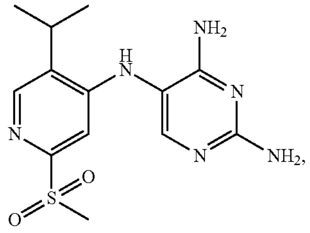
80
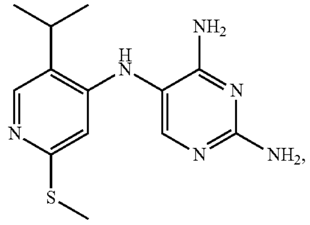
81
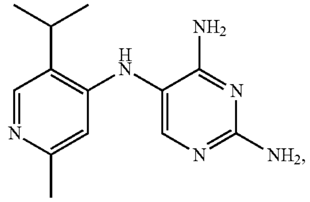
82
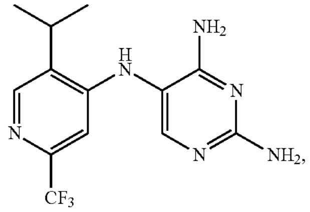
83
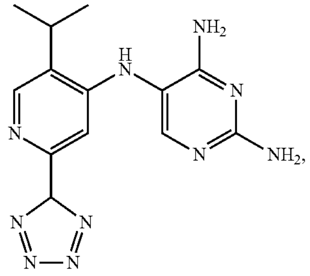
84
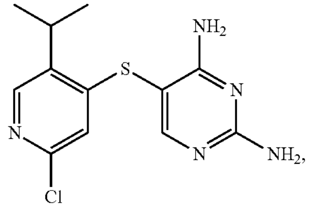
-continued
85
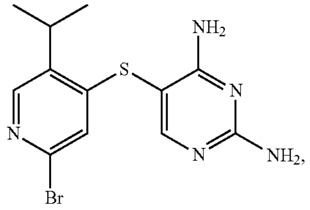
86
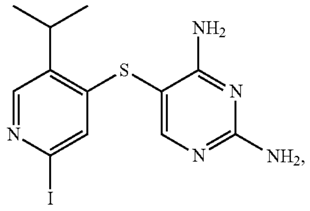
87
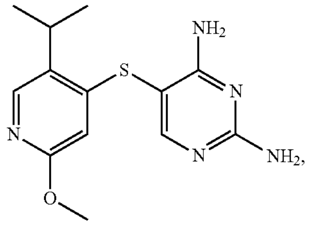
88
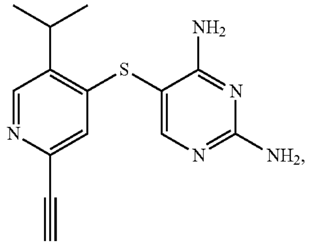
89
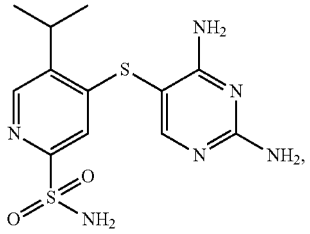
90
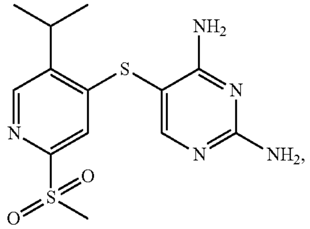
91
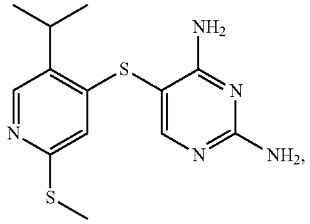

-continued
92
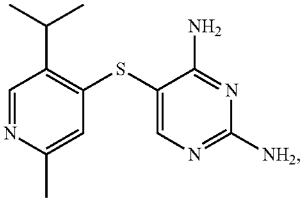
93
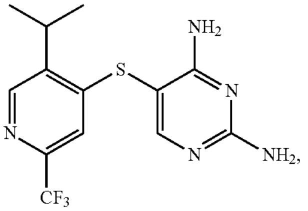
94
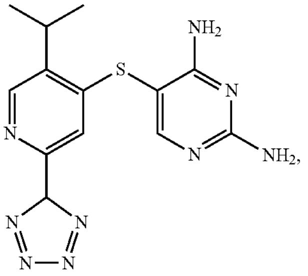
95
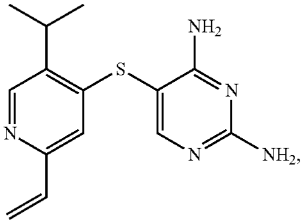
96
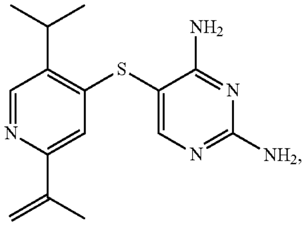
97
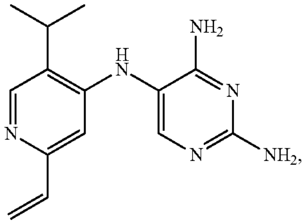
98
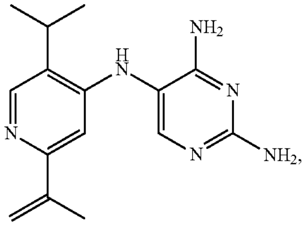
-continued
99
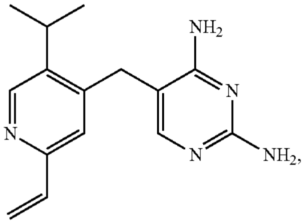
100
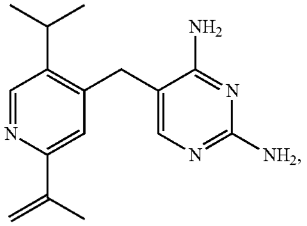
101
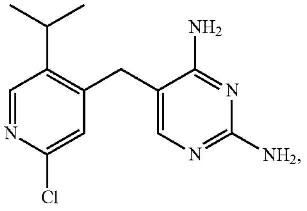
102
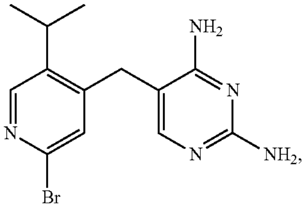
103
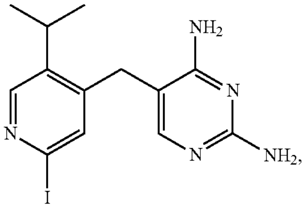
104
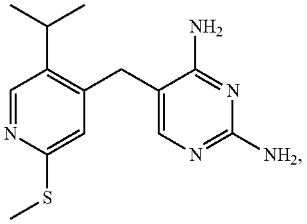
105
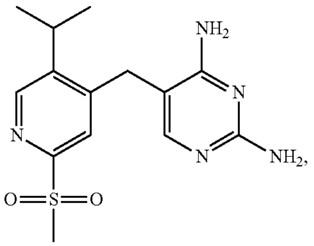

-continued
106
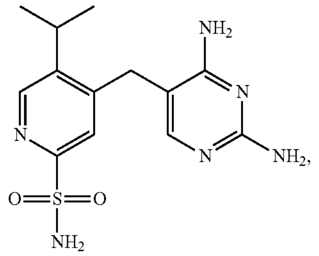
107
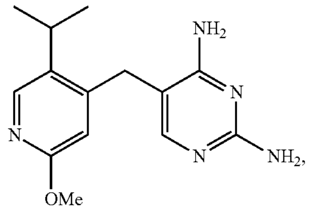
108
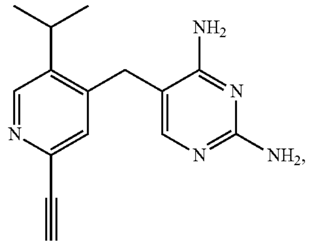
109
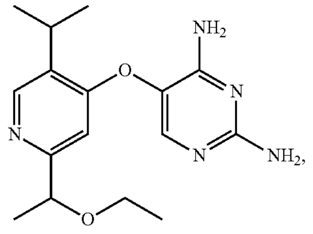
110
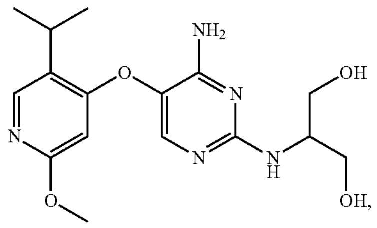
111
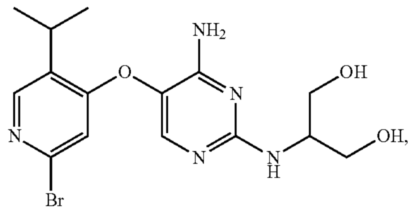
-continued
112
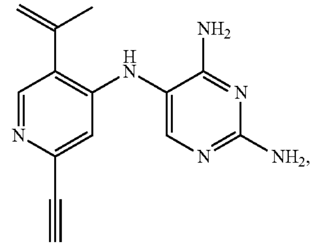
113
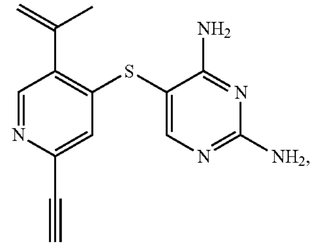
114
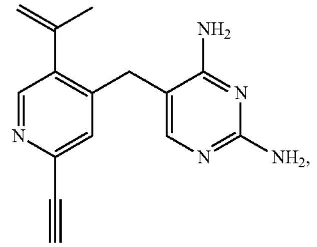
115
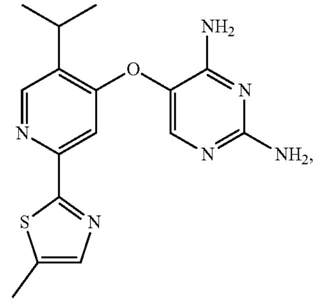
116
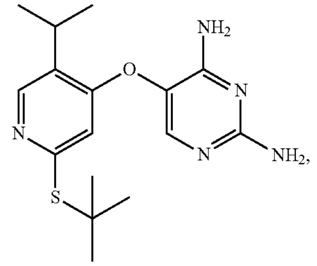
117
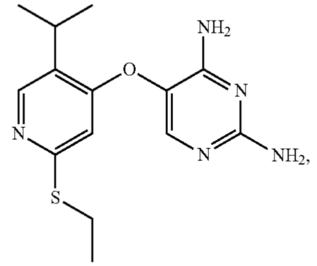

-continued
118
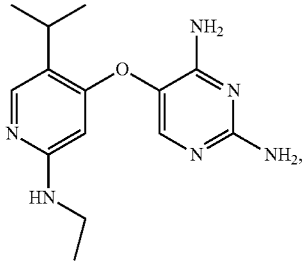
119
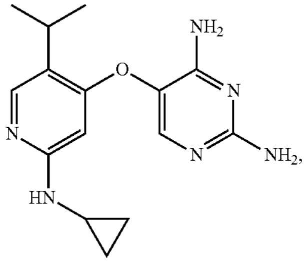
120
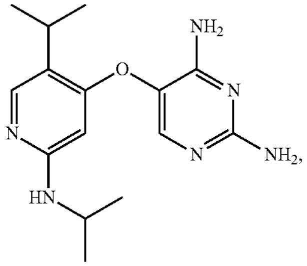
121
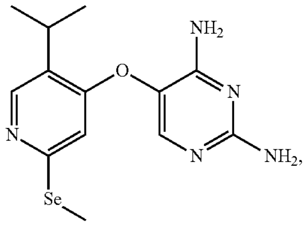
122
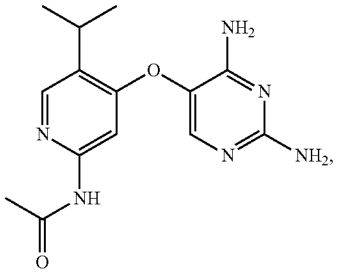
123
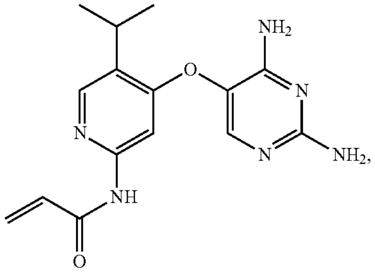
-continued
124
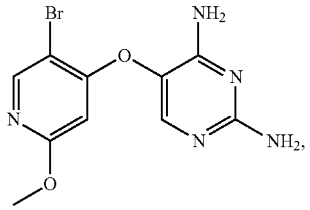
125
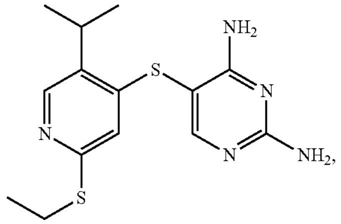
126
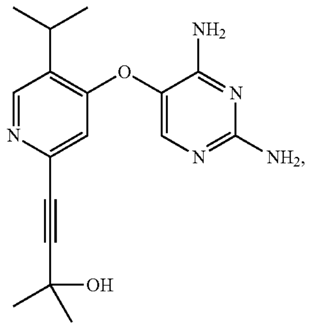
127
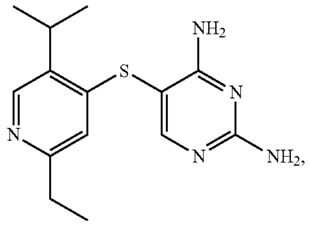
128
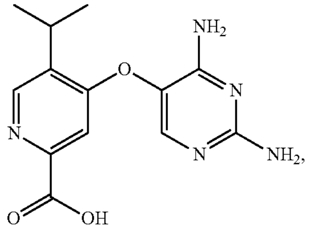
129
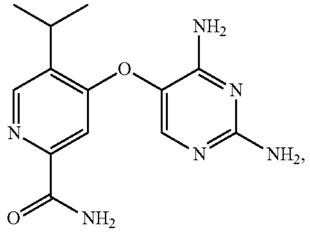

-continued
130
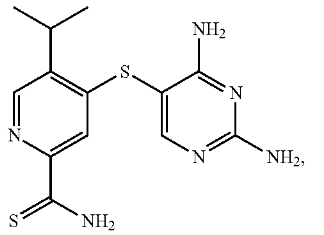
131
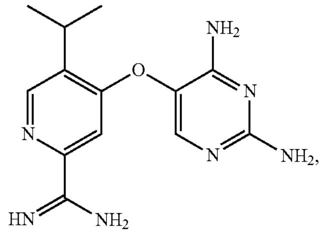
132
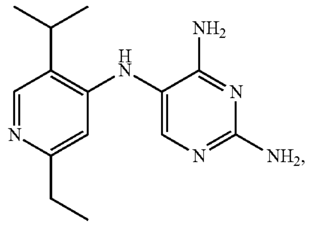
133
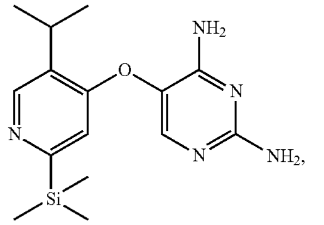
134
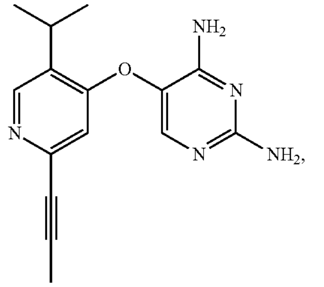
135
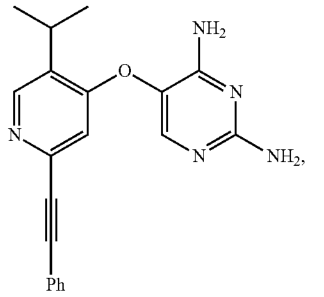
-continued
136
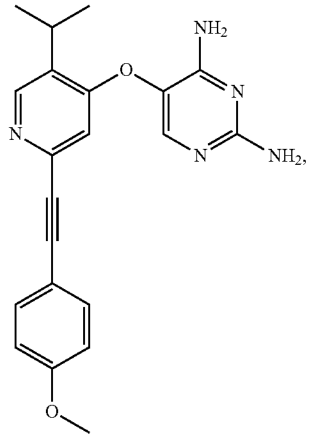
137
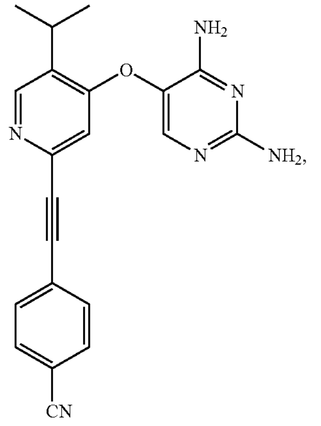
138
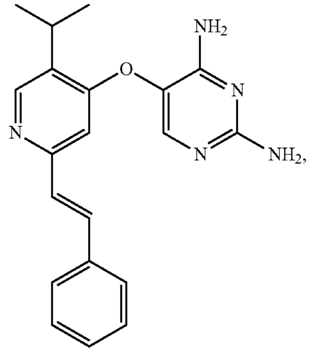
139
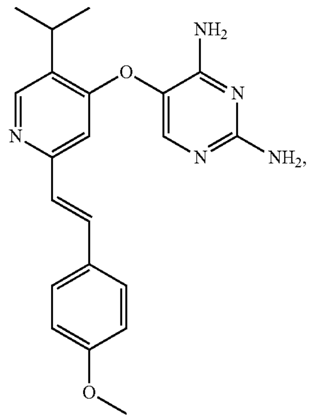

-continued
140
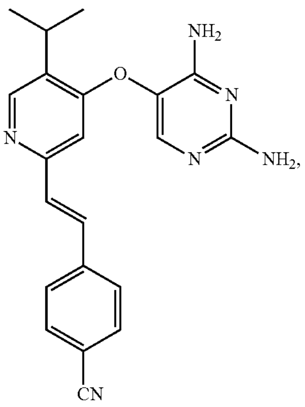
141
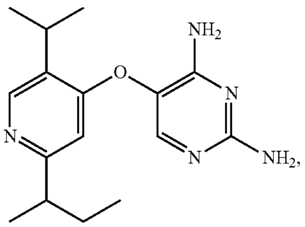
142
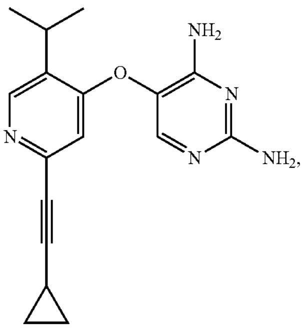
143
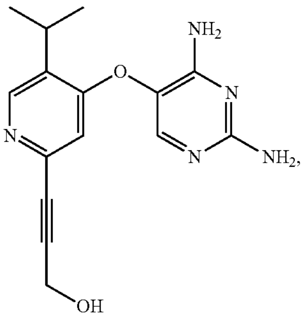
-continued
144
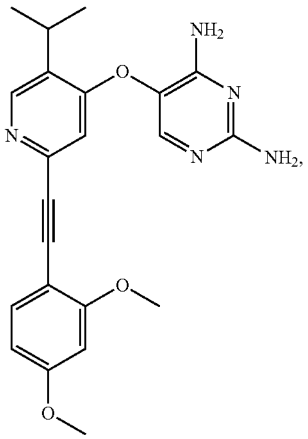
145
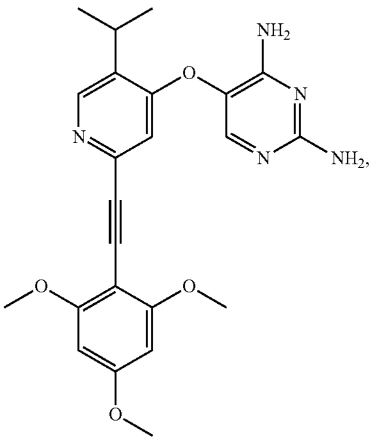
146
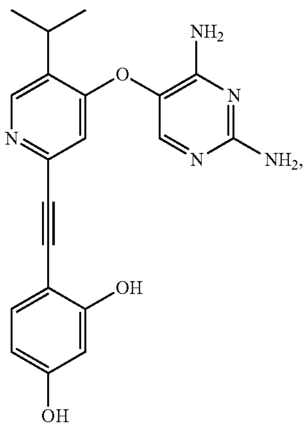

-continued
147
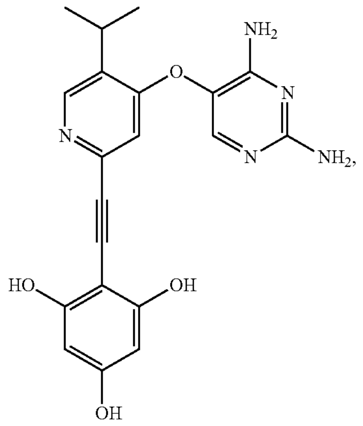
148
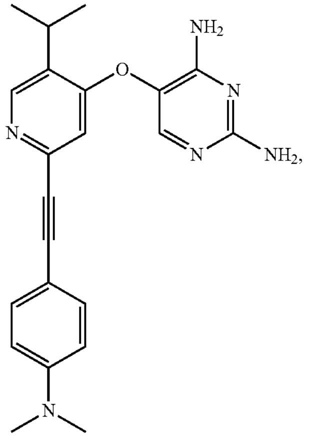
149
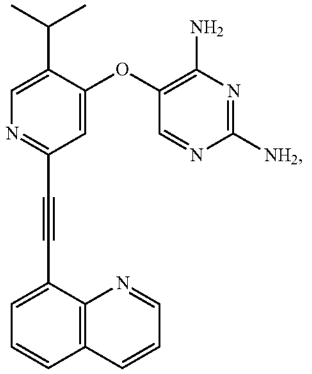
150
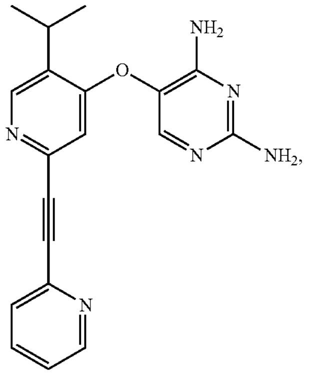
-continued
151
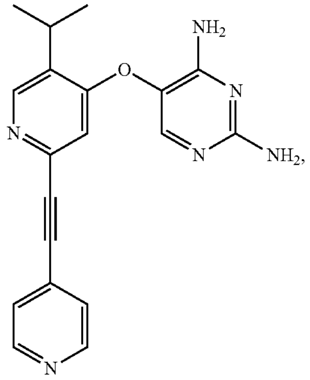
152
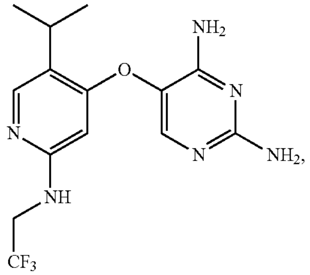
153
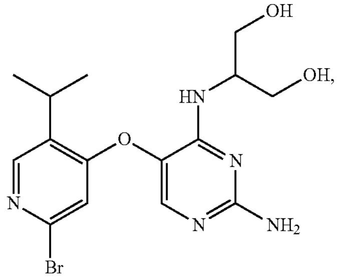
154
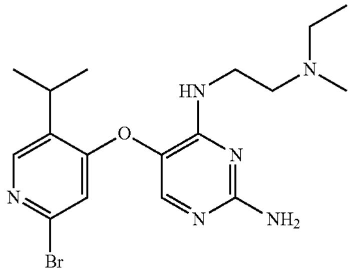
,
155
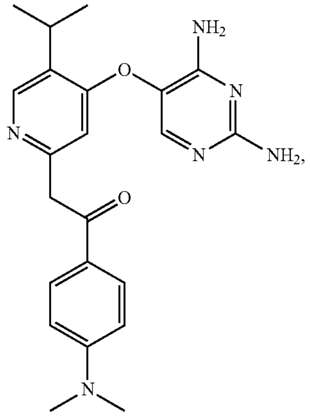

-continued
156
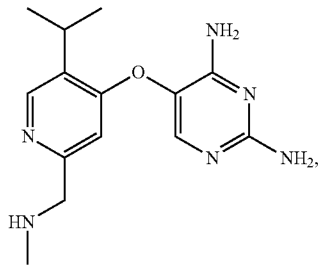
157
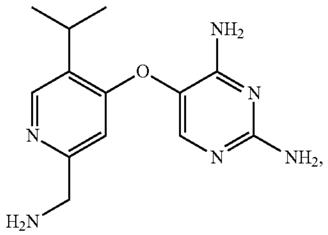
158
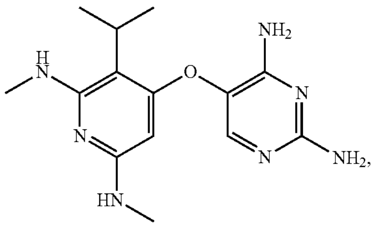
159
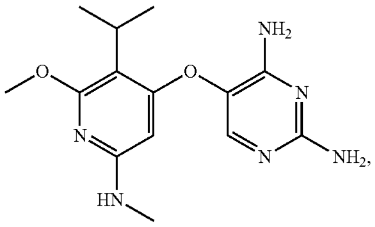
160
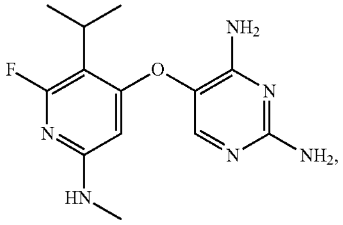
161
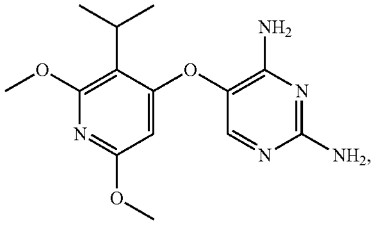
-continued
162
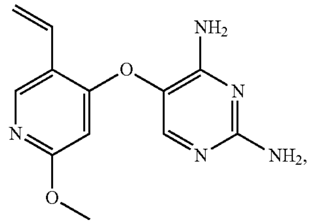
163
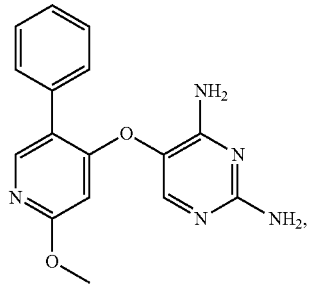
164
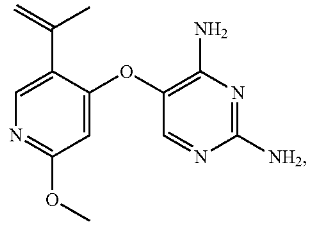
165
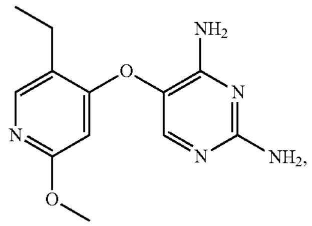
166
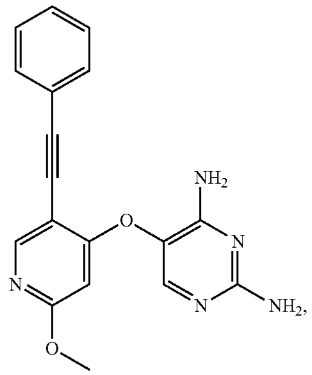
167
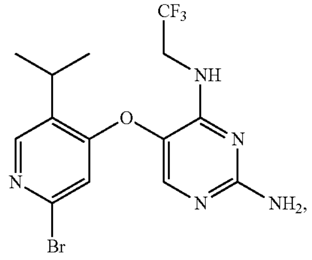

-continued
168
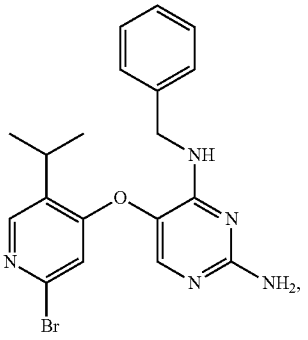
169
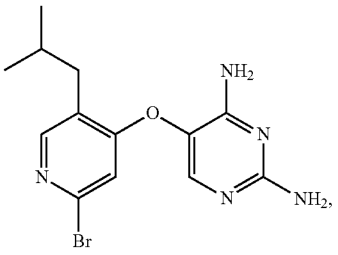
170
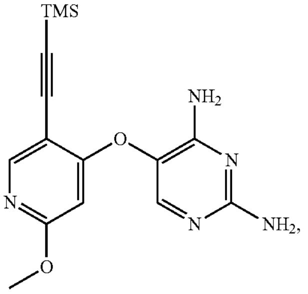
171
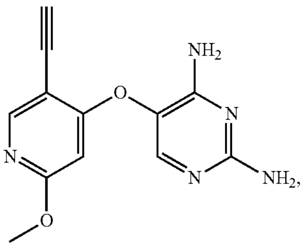
172
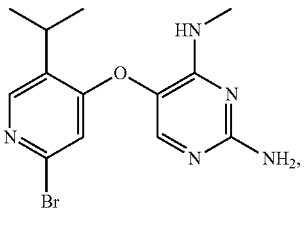
173
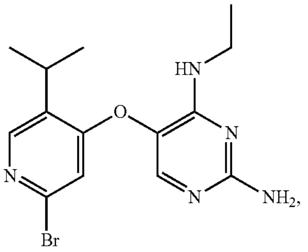
-continued
174
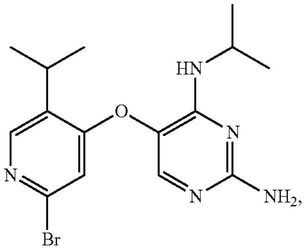
175
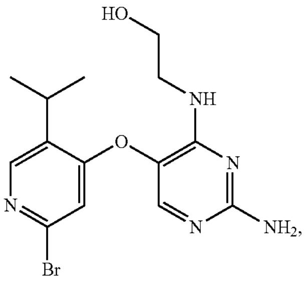
176
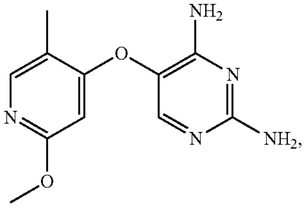
177
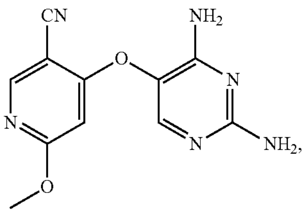
178
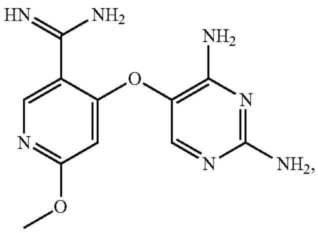
179
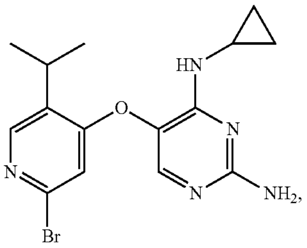

-continued
180
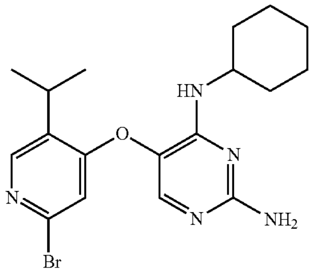
,
181
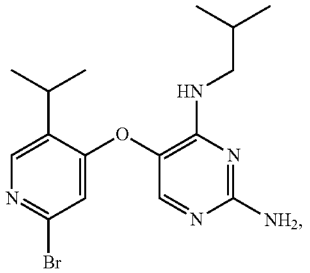
182
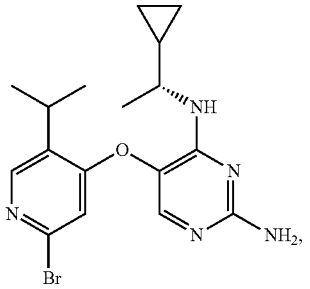
183
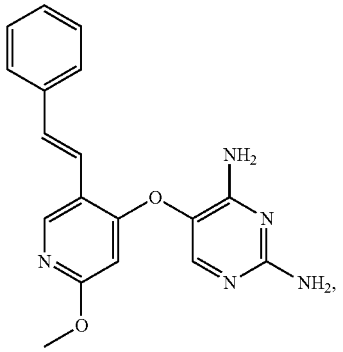
184
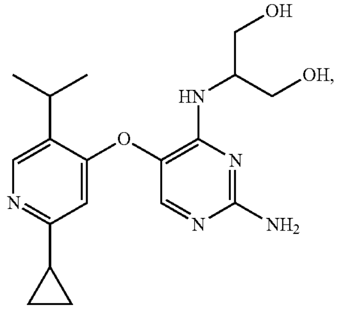
-continued
185
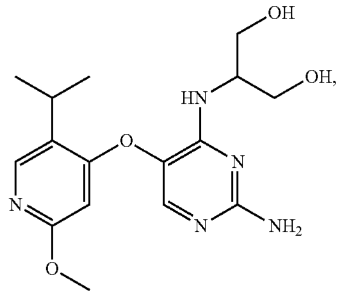
186
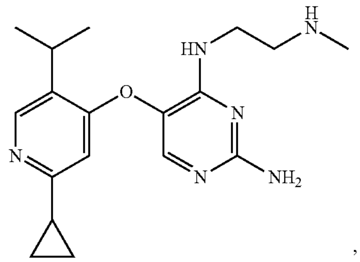
,
187
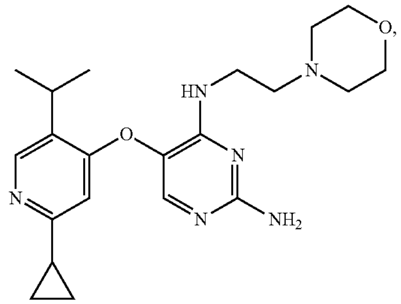
188
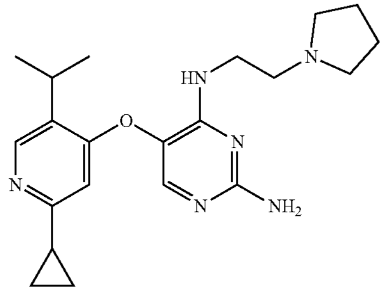
,
189
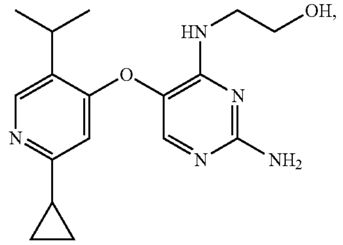

-continued
190
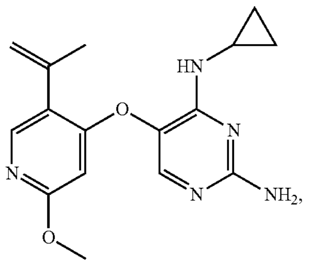
191
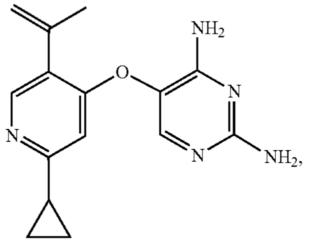
192
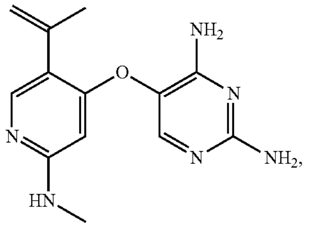
193
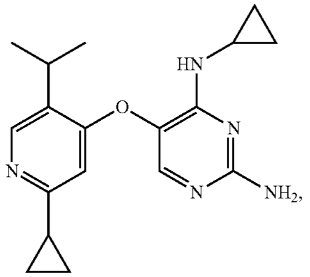
194
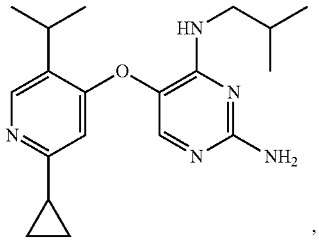
,
-continued
195
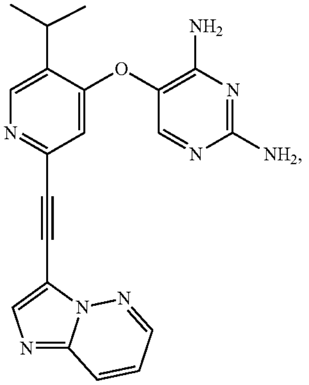
196
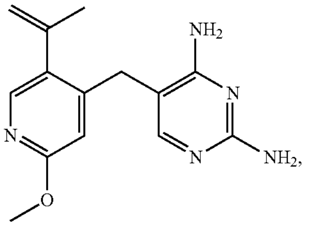
197
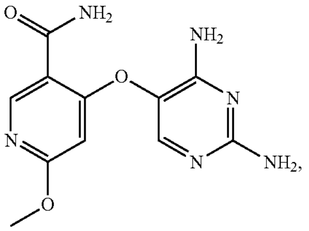
198
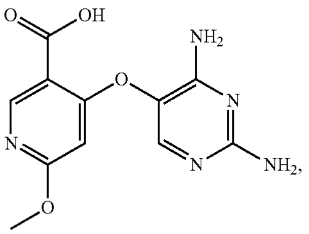
199
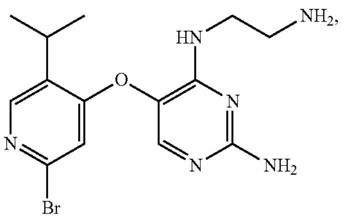
200
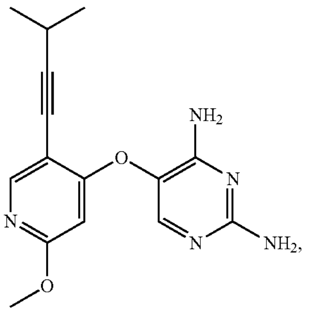

-continued
201
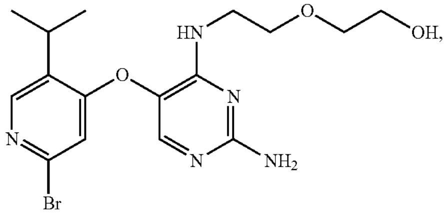
202
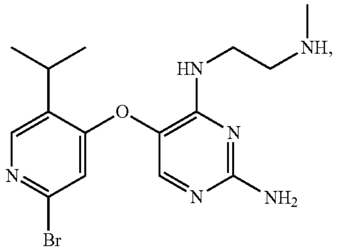
203
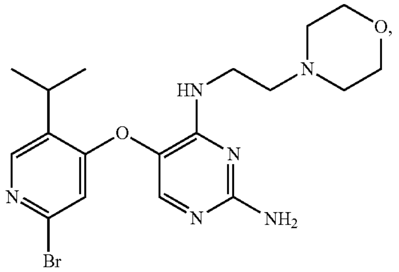
204
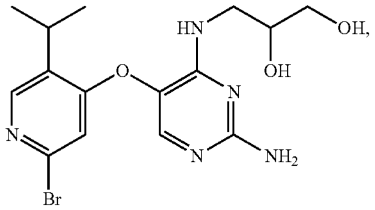
205
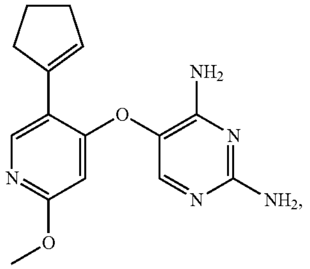
206
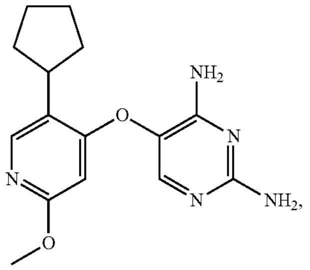
-continued
207
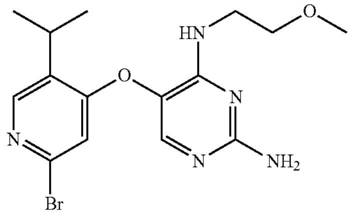
,
208
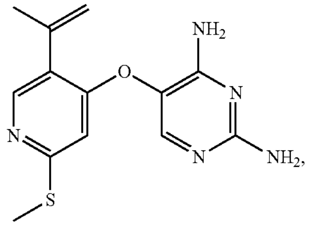
209
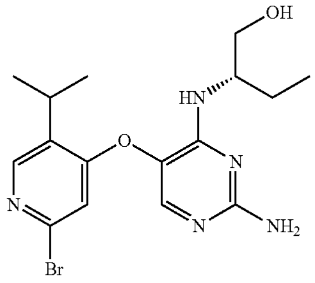
,
210
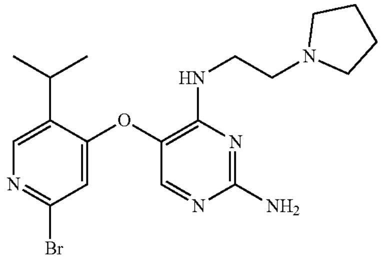
,
211
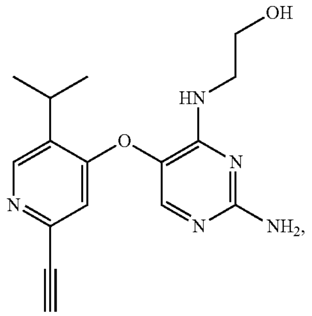
212
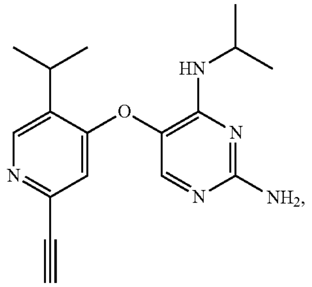

-continued
213
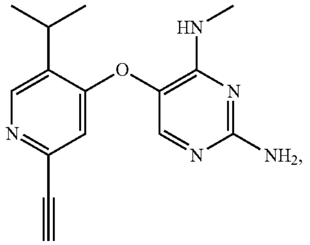
214
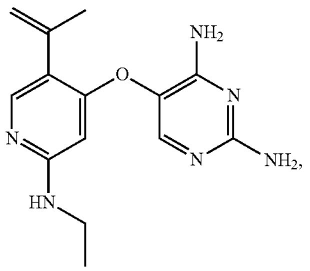
215
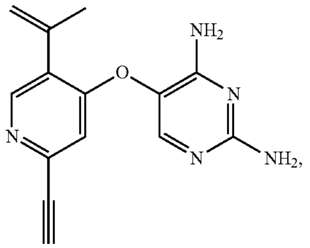
216
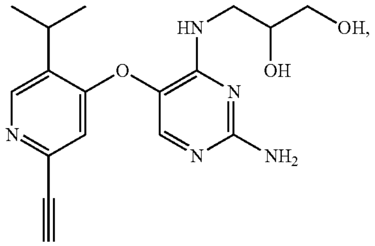
217
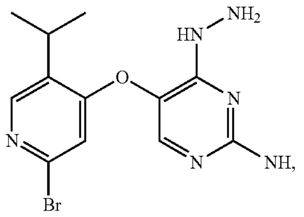
218
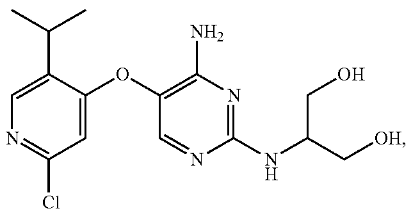
-continued
219
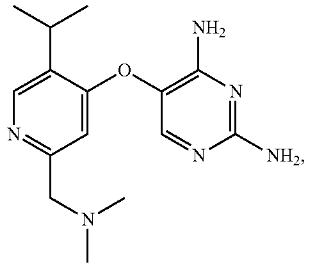
220
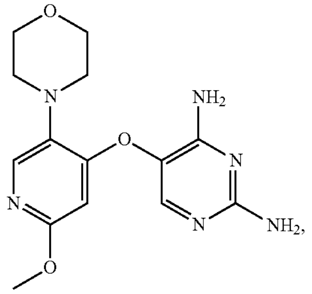
221
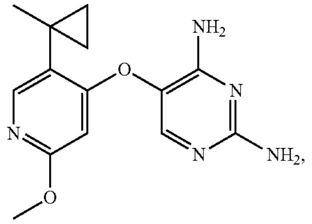
222
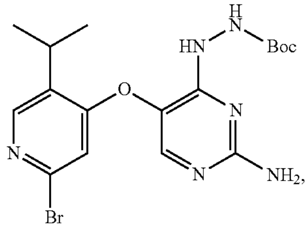
223
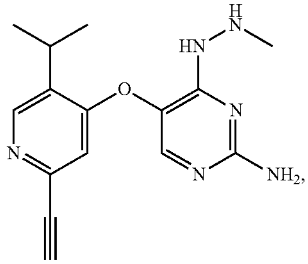
224
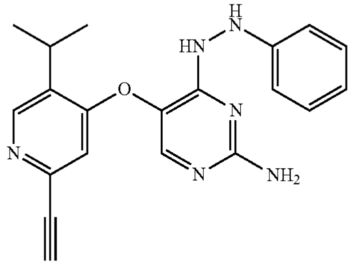
, -continued
225
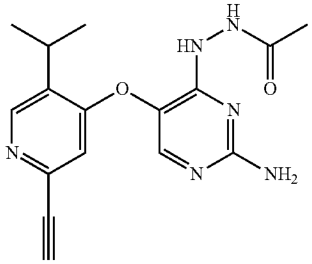
,
226
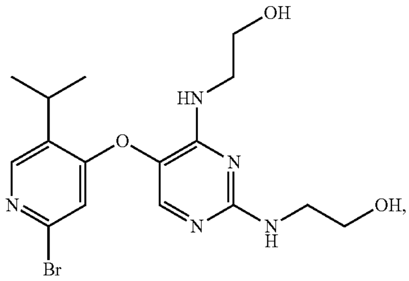
227
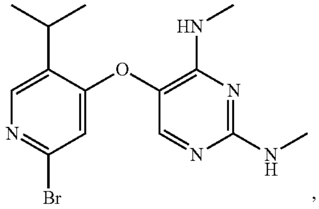
,
228
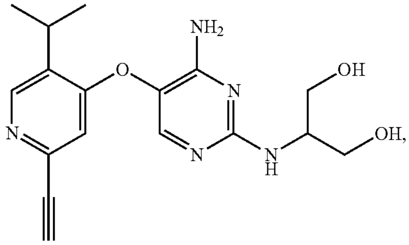
229
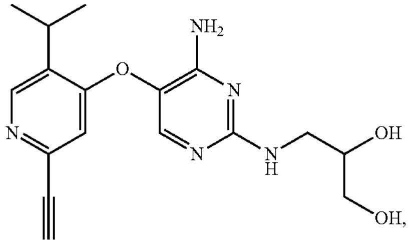
230
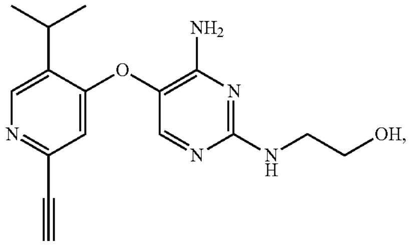
-continued
231
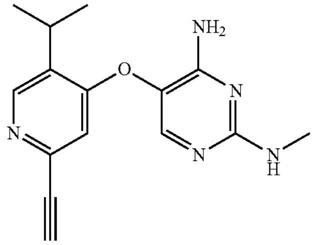
,
232
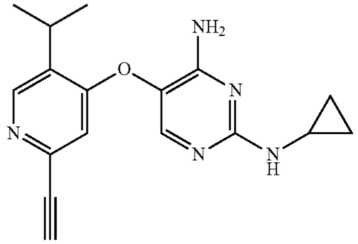
,
233
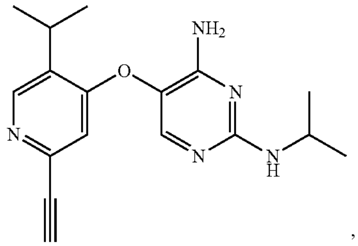
,
234
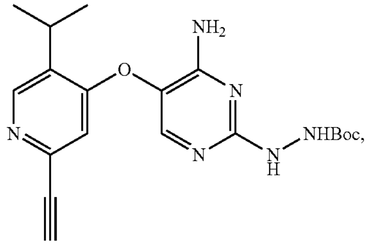
235
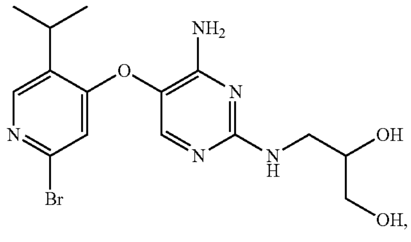
236
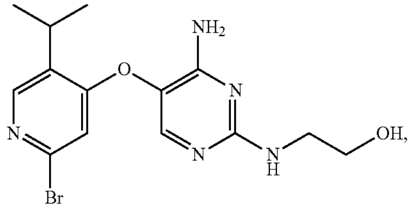

-continued

237

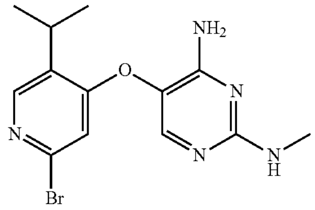

,

238

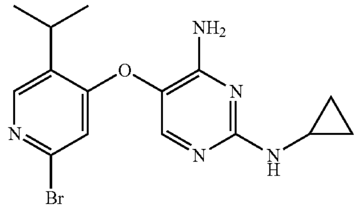

,

239

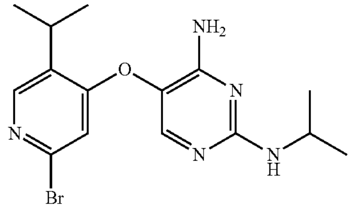

,

240

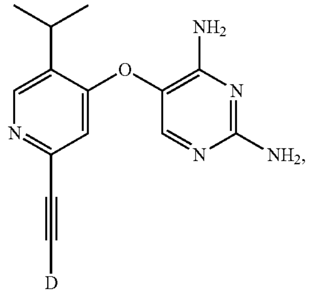

241

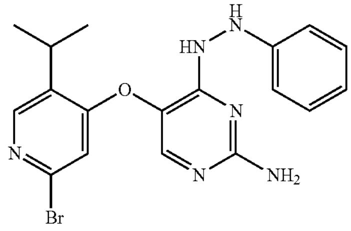

,

242

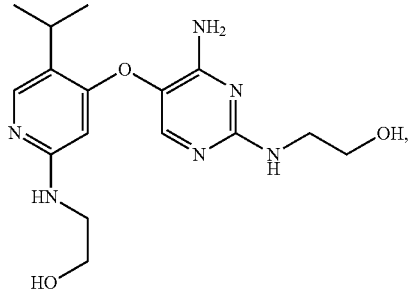

-continued

243

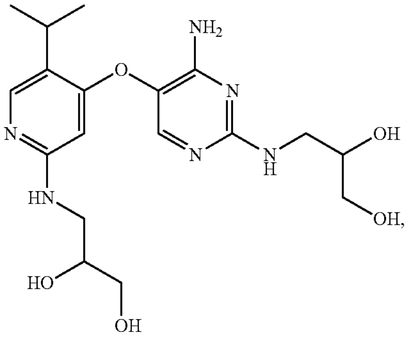

244

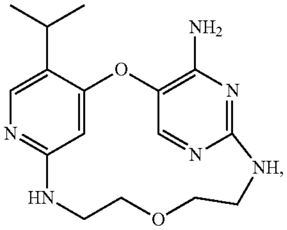

245

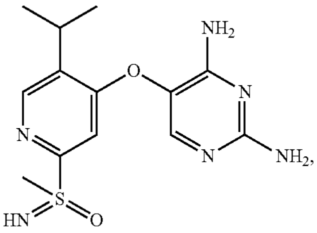

246

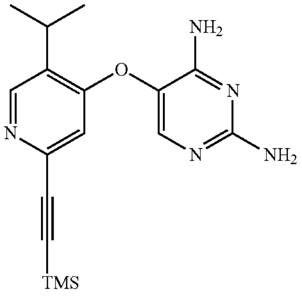

or

247

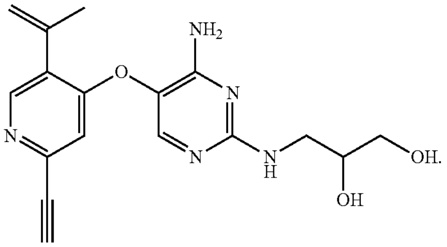

In some embodiments, the compound of Formula (I) or a pharmaceutically acceptable salt, ester, stereoisomer, polymorph, solvate, N-oxide, isotopically labeled compound, metabolite or prodrug thereof is administered in an amount of about 0.005 mg/day to about 5000 mg/day, e.g., in an amount of about 0.005, 0.05, 0.5, 5, 10, 20, 30, 40, 50, 100, 150, 200, 250, 300, 350, 400, 450, 500, 550, 600, 650, 700, 750, 800, 850, 900, 950, 1000, 1500, 2000, 2500, 3000, 3500, 4000, 4500 or 5000 mg/day.

In some embodiments, the compound of Formula (I) or a pharmaceutically acceptable salt, ester, stereoisomer, polymorph, solvate, N-oxide, isotopically labeled compound, metabolite or prodrug thereof is administered in an amount of about 1 ng/kg to about 200 mg/kg, about 1 μg/kg to about 100 mg/kg or about 1 mg/kg to about 50 mg/kg per day, e.g., is administered in an amount of about 1 μg/kg, about 10 μg/kg, about 25 μg/kg, about 50 μg/kg, about 75 μg/kg, about 100 μg/kg, about 125 μg/kg, about 150 μg/kg, about 175 μg/kg, about 200 μg/kg, about 225 μg/kg, about 250 μg/kg, about 275 μg/kg, about 300 μg/kg, about 325 μg/kg, about 350 μg/kg, about 375 μg/kg, about 400 μg/kg, about 425 μg/kg, about 450 μg/kg, about 475 μg/kg, about 500 μg/kg, about 525 μg/kg, about 550 μg/kg, about 575 μg/kg, about 600 μg/kg, about 625 μg/kg, about 650 μg/kg, about 675 μg/kg, about 700 μg/kg, about 725 μg/kg, about 750 μg/kg, about 775 μg/kg, about 800 μg/kg, about 825 μg/kg, about 850 μg/kg, about 875 μg/kg, about 900 μg/kg, about 925 μg/kg, about 950 μg/kg, about 975 μg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg body weight per unit dose.

In some embodiments, the daily dose of the compound of Formula (I) or a pharmaceutically acceptable salt, ester, stereoisomer, polymorph, solvate, N-oxide, isotopically labeled compound, metabolite or prodrug thereof is administered at one time or is administered in two, three or four doses.

In some embodiments, the compound of Formula (I) or a pharmaceutically acceptable salt, ester, stereoisomer, polymorph, solvate, N-oxide, isotopically labeled compound, metabolite or prodrug thereof is administered continuously for at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days, at least 50 days, at least half a year, at least 1 year, at least 2 years, at least 3 years, at least 4 years, at least 5 years or more years.

In some embodiments, the compound of Formula (I) or a pharmaceutically acceptable salt, ester, stereoisomer, polymorph, solvate, N-oxide, isotopically labeled compound, metabolite or prodrug thereof is administered for one or more (e.g., 1, 2, 3, 4, 5, 6, 7, 8, 9 or 10) courses of treatment, wherein each course of treatment lasts for at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days or at least 50 days; and the interval between every two courses of treatment is 0, 1, 2, 3, 4, 5, 6, 7, 8, 9, 10 days, two weeks, three weeks, or four weeks.

In some embodiments, the compound of Formula (I) or a pharmaceutically acceptable salt, ester, stereoisomer, polymorph, solvate, N-oxide, isotopically labeled compound, metabolite or prodrug thereof is administered through injection (e.g., intravenous, intraarterial, subcutaneous, intraperitoneal, intramuscular injection, including dripping), or transdermal administration, or is administered via oral, buccal, nasal, transmucosal, or topical route, as an ophthalmic formulation, or via inhalation.

In some embodiments, the compound of Formula (I) or a pharmaceutically acceptable salt, ester, stereoisomer, polymorph, solvate, N-oxide, isotopically labeled compound, metabolite or prodrug thereof is administered in a dosage form selected from the group consisting of tablet, capsule, lozenge, hard candy, powder, spray, emulsion, cream, salve, suppository, gel, paste, lotion, injection, nanoformulation, patch, aqueous suspension, injectable solution, elixir, and syrup.

In some embodiments, the endometriosis-associated pain is selected from one or more of endometriosis-induced chronic pelvic pain, menstrual pain, pain with intercourse, low back pain, abdominal pain, vagina pain, visceral organ pain, and painful bowel movements and/or painful urination during menstruation.

EXAMPLE

In order to make the objects and technical solutions of the invention clearer, the invention will be further described below with reference to specific examples. It should be understood that the following examples are only intended for illustrating the invention and are not to be understood as limiting the scope of the invention. Further, specific experimental methods not mentioned in the following examples are carried out in accordance with conventional experimental methods.

Unless otherwise stated, the reagents employed in the following examples were purchased from companies such as Aladdin, Shanghai Accela ChemBio Co., Ltd., Alfa Aesar, Sinopharm Chemical Reagent Co., Ltd., etc.

Compound 66 of the present application was prepared according to the method described in PCT/CN2018/112829 (which is incorporated herein by reference in its entirety).

Example 1

Hot Plate Test on Autotransplantation-Induced Endometriosis Model Rats

Animal: Sexually mature unmated female SPF grade Sprague-Dawley rats from about 8 to 12 weeks old (200-220 g) were purchased from Beijing Vital River Laboratory Animal Technology Co., Ltd. Estrous rats were chosen through a vaginal smear examination.

Feeding: the rats were fed with a 12-hour light/12-hour dark cycle.

Surgical modeling: rats was deprived of food but not water at the night before surgery. The surgery was performed with ketamine hydrochloride (73 mg/kg) and xylazine (8.8 mg/kg) as anesthetics under sterile conditions. The rat abdomen was cut open along the midline to expose the uterus. About 1 cm of tissue was cut out from the left horn of uterus and the connected fat tissue, and the broken end was ligated. The 1 cm of horn of uterus was immersed in a sterile lactic acid solution, so that the horn of uterus was expanded longitudinally. Each horn of uterus was cut into 4 parts (each approximately 2.5 mm×2.5 mm). One piece of peeled uterine tissue was sewn to the inferior wall of the peritoneum with a 6/0 braided silk suture, so that the endometrial surface was appressed to the peritoneum. Among the remaining 3 pieces of peeled uterine tissue, one was sewn to the mesentery, one was sewn to the bifurcation of the uterus, and another one was sewn at the vicinity of the right ovary. The incision was sutured, and the endometrial tissue was collected and sent for pathological examination to confirm that it was endometrium.

Hot plate test: rats were randomly divided into three groups four weeks after the surgery, and a vehicle (0.5% CMC-Na), 120 mg/kg compound 66, and 60 mg/kg positive control ibuprofen were orally administered to each group. A hot plate test was performed within 1-2 hours after the administration, to determine the pain thresholds, and the time for the rat to lift or lick the hind paw for the first time was recorded. The average value of four recorded values was taken as the pain threshold of a rat.

Autopsy: The abdomen was cut open along the previous suture to check the physical condition of the transplanted tissue and abdominal organs. The criteria for successful model construction were as follows: cystic growth and enlargement of the graft were visible to the naked eyes; new blood vessels and a little connective tissue formed on the cyst wall, and cool or yellow liquid existed in the cyst; and the graft, after being fixed in a paraffin section and subjected to HE staining, were demonstrated to be rat endometrial tissue by a histopathologic examination.

Successfully modeled rats were included in a statistics group (12 animals in the vehicle group, 11 animals in the test group, and 13 animals in the control group). The results were analyzed by one-way ANONA Dunnett's multiple comparison method using Graphpad Prism software ( indicating $p<0.01$, and * indicating $p<0.001$). The results are shown in FIG. 1.

The results showed that the pain threshold of the rats in the test group was significantly higher than the pain thresholds of the rats in the vehicle group and the control group, indicating that the compound of the present invention suppressed and alleviated the endometriosis-associated pain.

Example 2. Inhibition on the P2X3-Mediated Current in 1321N1 Cell Line Stably Transfected with P2X3

Figure 2:
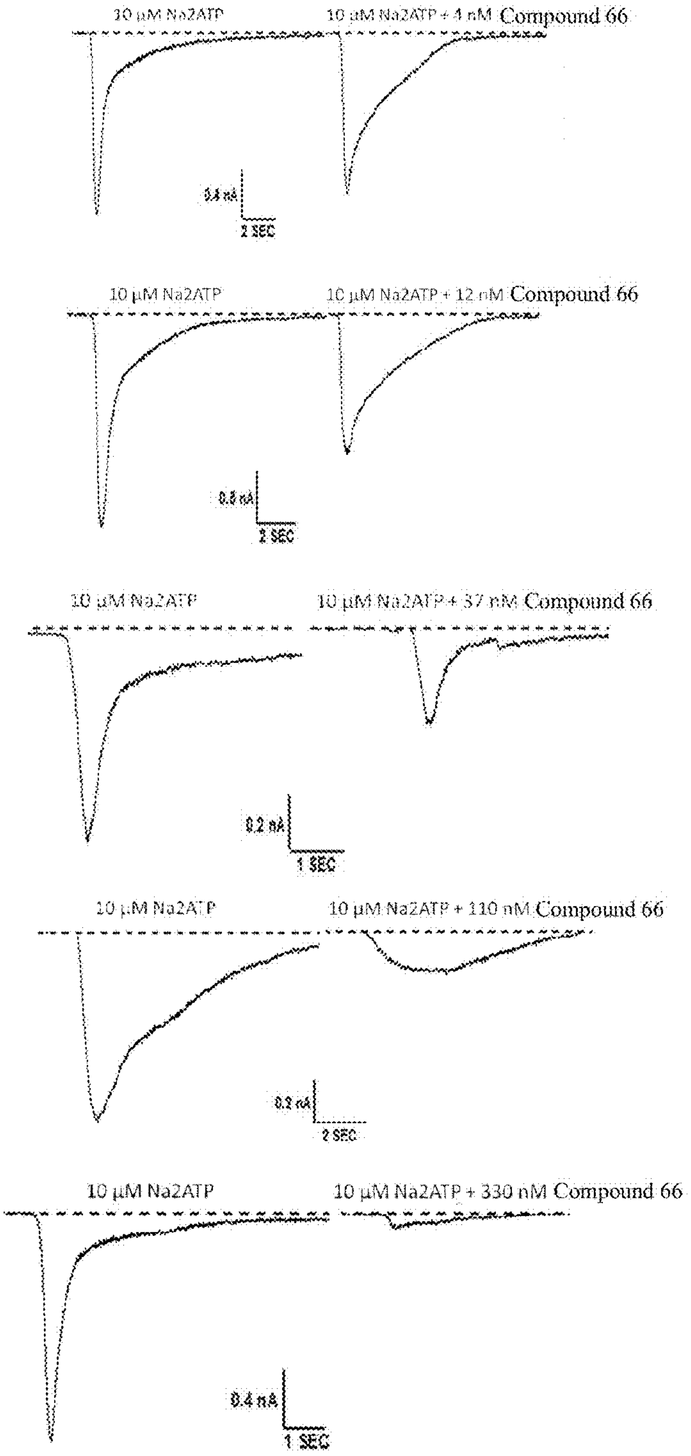
FIG. 2 shows the effect of compound 66 on the P2X3-mediated current in 1321N1 cells stably transfected with P2X3.

Membrane current was recorded by employing HEKA EPC-10 patch clamp amplifier and PATCHMASTER acquisition system. 1321N1 P2X3 stable transfected cells were transferred to an about 1 ml bath embedded in an inverted microscope platform, and an extracellular fluid (2 mM $CaCl_2$, 1 mM $MgCl_2$, 5 mM KCl, 155 mM NaCl, 12 mM glucose and 10 mM HEPES (pH=7.4)) was perfused by using a gravitational perfusion system. The P2X3-mediated current of a single cell was recorded in a whole cell recording mode. After formation of a gigaseal and rapture of the membrane, clamping potential was set at −60 mV. 10 μM Na2ATP was perfused for 5 seconds, and the P2X3-mediated current induced at this point was taken as a control current. The cells were then treated with a solution of compound 66 at a specific concentration (prepared with the extracellular fluid) for 5 minutes. The solution of compound 66 at this concentration and 10 μM Na2ATP were co-applied to induce a cell current (see FIG. 2 for the effect of the compound on the current), and an inhibition rate relative to the control current was calculated according to the following formula:

$$\text{Inhibition Rate Relative to the Control Current}=(1-I_2/I_1)*100\%$$

wherein $I_1$ represents the control current, and $I_2$ represents the current after application of compound 66. The concentrations of the test compound 66 included 4, 12, 37, 110 and 330 nM, and at least three cells (n≥3) were tested at each concentration.

Figure 3:
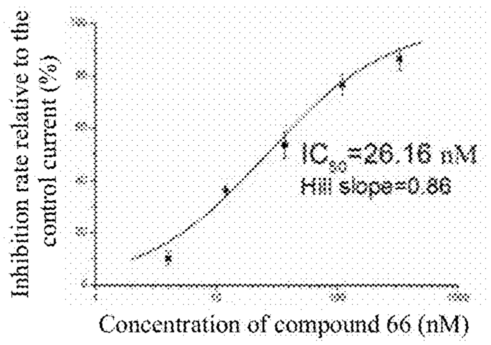
FIG. 3 shows the concentration-inhibition curve of compound 66 on the P2X3-mediated current in 1321N1 cells stably transfected with P2X3.

The concentration of compound 66 (as the horizontal axis) was plotted against the inhibition rate relative to the control current (as the vertical axis) (see FIG. 3), and the data were fitted with the Hill equation to obtain that the concentration required for compound 66 to inhibit the P2X3-mediated current induced by 10 μM Na2ATP by 50% ($IC_{50}$) was 26.16 nM.

Example 3. Inhibition on the P2X3-Mediated Current in Ex Vivo Cultured Rat Dorsal Root Ganglion (DRG)

Figure 4:
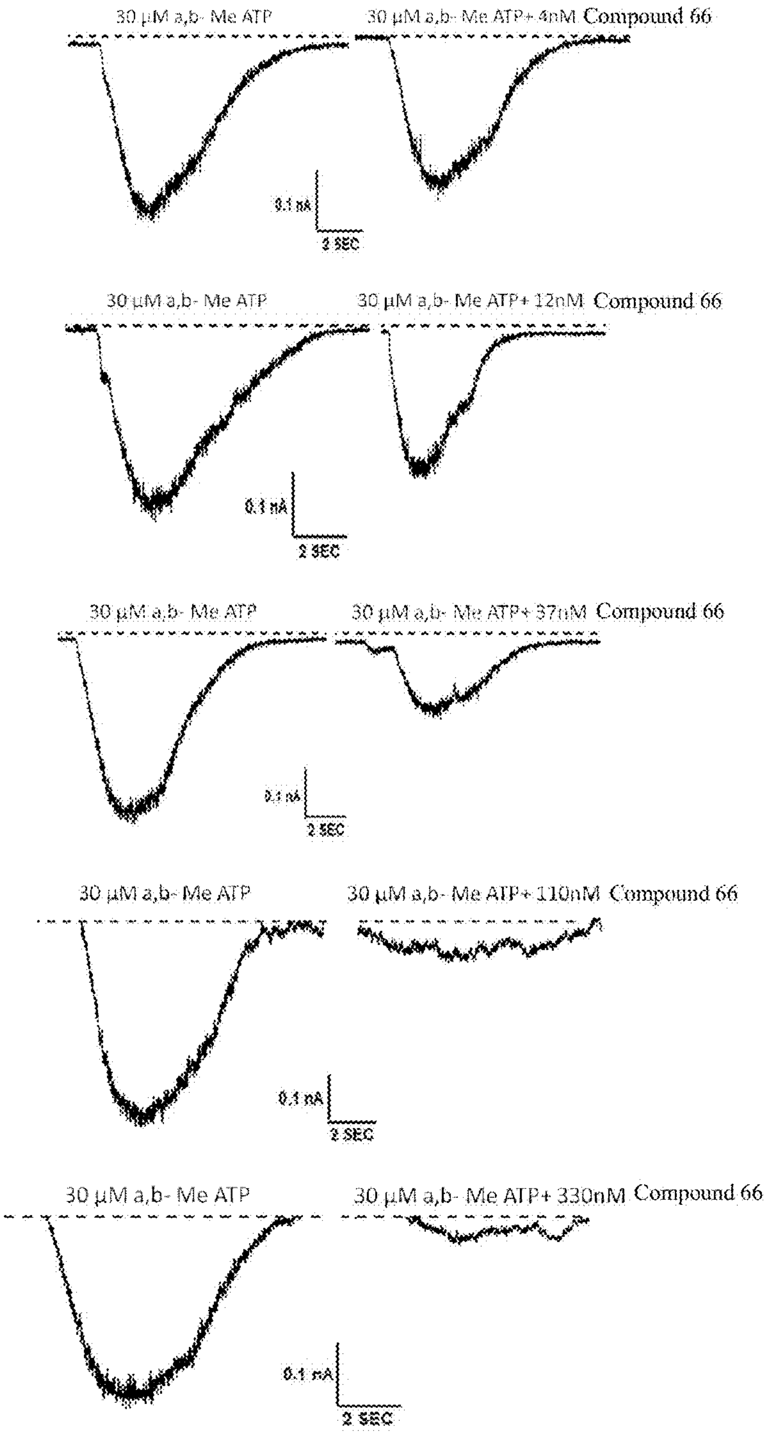
FIG. 4 shows the effect of compound 66 on the P2X3-mediated current in rat dorsal root ganglion cells.

Membrane current was recorded by employing HEKA EPC-10 patch clamp amplifier and PATCHMASTER acquisition system. The primary cells of rat DRG were transferred to an about 1 ml bath embedded in an inverted microscope platform, and an extracellular fluid (2 mM $CaCl_2$, 1 mM $MgCl_2$, 5 mM KCl, 155 mM NaCl, 12 mM glucose and 10 mM HEPES (pH=7.4)) was perfused by using a gravitational perfusion system. The P2X3-mediated current of a single cell was recorded in a whole cell recording mode. After formation of a gigaseal and rapture of the membrane, clamping potential was set at −60 mV. 30 μM a,b-Me ATP (also known as "α,β-meATP") was perfused for 5 seconds, and the P2X3-mediated current induced at this point was taken as a control current. The cells were then treated with a solution of compound 66 at a specific concentration (prepared with the extracellular fluid) for 5 minutes. The solution of compound 66 at this concentration and 30 μM a,b-Me ATP were co-applied to induce a cell current (see FIG. 4 for the effect of the compound on the current), and an inhibition rate relative to the control current was calculated according to the following formula:

$$\text{Inhibition Rate Relative to the Control Current}=(1-I_2/I_1)*100\%$$

wherein $I_1$ represents the control current, and $I_2$ represents the current after application of compound 66. The concentrations of the test compound 66 included 4, 12, 37, 110 and 330 nM, and at least three cells (n≥3) were tested at each concentration.

Figure 5:
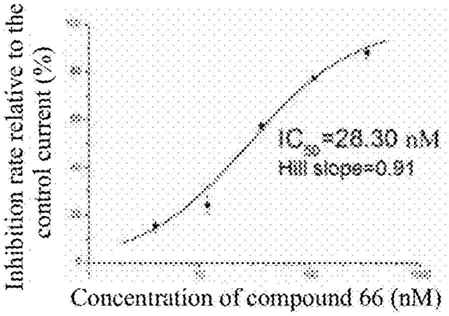
FIG. 5 shows the concentration-inhibition curve of compound 66 on the P2X3-mediated current in rat dorsal root ganglion cells.

The concentration of compound 66 (as the horizontal axis) was plotted against the inhibition rate relative to the control current (as the vertical axis) (see FIG. 5), and the data were fitted with the Hill equation to obtain that the concentration required for compound 66 to inhibit the P2X3-mediated current induced by 30 μM a,b-Me ATP by 50% ($IC_{50}$) was 28.30 nM.

Various modifications to the invention in addition to those described herein will become apparent to those skilled in the art from the foregoing description. Such modifications are intended to fall within the scope of the appended claims Each reference, including all patents, applications, journal articles, books and any other disclosure, referred to herein is hereby incorporated by reference in its entirety.

What is claimed is:

1. A method for treating, suppressing or alleviating endometriosis-associated pain, comprising administering to a subject in need of treating, suppressing or alleviating endometriosis-associated pain a therapeutically effective amount of compound 66 or a pharmaceutically acceptable salt, ester, stereoisomer, polymorph, solvate, N-oxide, isotopically labeled compound or prodrug thereof:

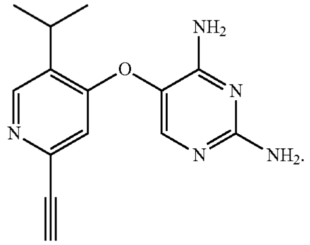

66

2. The method according to claim 1, wherein the compound or a pharmaceutically acceptable salt, ester, stereoisomer, polymorph, solvate, N-oxide, isotopically labeled compound or prodrug thereof is administered in a therapeutically effective amount of 0.005 mg/day to 5000 mg/day.

3. The method according to claim 2, wherein the compound or a pharmaceutically acceptable salt, ester, stereoisomer, polymorph, solvate, N-oxide, isotopically labeled compound or prodrug thereof is administered in a therapeutically effective amount selected from one of:

0.005, 0.05, 0.5, 5, 10, 20, 30, 40, 50, 100, 150, 200, 250, 300, 350, 400, 450, 500, 550, 600, 650, 700, 750, 800, 850, 900, 950, 1000, 1500, 2000, 2500, 3000, 3500, 4000, 4500 or 5000 mg/day.

4. The method according to claim 1, wherein the compound or a pharmaceutically acceptable salt, ester, stereoisomer, polymorph, solvate, N-oxide, isotopically labeled compound or prodrug thereof is administered in a therapeutically effective amount selected from one of:

1 ng/kg to 200 mg/kg, 1 g/kg to 100 mg/kg, or 1 mg/kg to 50 mg/kg body weight per day.

5. The method according to claim 1, wherein the compound or a pharmaceutically acceptable salt, ester, stereoisomer, polymorph, solvate, N-oxide, isotopically labeled compound or prodrug thereof is administered in a therapeutically effective amount selected from one of:

1 μg/kg, 10 μg/kg, 25 μg/kg, 50 μg/kg, 75 μg/kg, 100 μg/kg, 125 μg/kg, 150 μg/kg, 175 μg/kg, 200 μg/kg, 225 μg/kg, 250 μg/kg, 275 μg/kg, 300 μg/kg, 325 μg/kg, 350 μg/kg, 375 μg/kg, 400 μg/kg, 425 μg/kg, 450 μg/kg, 475 μg/kg, 500 μg/kg, 525 μg/kg, 550 μg/kg, 575 μg/kg, 600 μg/kg, 625 μg/kg, 650 μg/kg, 675 μg/kg, 700 μg/kg, 725 μg/kg, 750 μg/kg, 775 μg/kg, 800 μg/kg, 825 μg/kg, 850 μg/kg, 875 μg/kg, 900 μg/kg, 925 μg/kg, 950 μg/kg, 975 μg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg body weight per unit dose.

6. The method according to claim 1, wherein the therapeutically effective amount of the compound or a pharmaceutically acceptable salt, ester, stereoisomer, polymorph, solvate, N-oxide, isotopically labeled compound or prodrug thereof is administered at one time or is administered in two, three or four doses.

7. The method according to claim 1, wherein the compound or a pharmaceutically acceptable salt, ester, stereoisomer, polymorph, solvate, N-oxide, isotopically labeled compound or prodrug thereof is administered continuously for a time selected from one of:

at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days, at least 50 days, at least half a year, at least 1 year, at least 2 years, at least 3 years, at least 4 years, or at least 5 years.

8. The method according to claim 1, wherein the compound or a pharmaceutically acceptable salt, ester, stereoisomer, polymorph, solvate, N-oxide, isotopically labeled compound or prodrug thereof is administered for one or more courses of treatment, wherein each course of treatment is for a time period selected from one of the following:

at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 30 days, at least 35 days, at least 40 days, at least 45 days or at least 50 days; and wherein the interval between every two courses of treatment is selected from one of:

0, 1, 2, 3, 4, 5, 6, 7, 8, 9, 10 days, two weeks, three weeks, or four weeks.

9. The method according to claim 8, wherein the compound or a pharmaceutically acceptable salt, ester, stereoisomer, polymorph, solvate, N-oxide, isotopically labeled compound or prodrug thereof is administered for 1, 2, 3, 4, 5, 6, 7, 8, 9 or 10 courses of treatment.

10. The method according to claim 1, wherein the compound or a pharmaceutically acceptable salt, ester, stereoisomer, polymorph, solvate, N-oxide, isotopically labeled compound or prodrug thereof is administered through injection, or transdermal administration, or is administered via oral, buccal, nasal, transmucosal, or topical route, as an ophthalmic formulation, or via inhalation.

11. The method according to claim 10, wherein the compound or a pharmaceutically acceptable salt, ester, stereoisomer, polymorph, solvate, N-oxide, isotopically labeled compound or prodrug thereof is administered through intravenous, intraarterial, subcutaneous, intraperitoneal, or intramuscular injection.

12. The method according to claim 10, wherein the compound or a pharmaceutically acceptable salt, ester, stereoisomer, polymorph, solvate, N-oxide, isotopically labeled compound or prodrug thereof is administered through dripping injection.

13. The method according to claim 1, wherein the compound or a pharmaceutically acceptable salt, ester, stereoisomer, polymorph, solvate, N-oxide, isotopically labeled compound or prodrug thereof is administered in a dosage form selected from the group consisting of a tablet, capsule, lozenge, hard candy, powder, spray, emulsion, cream, salve, suppository, gel, paste, lotion, injection, nanoformulation, patch, aqueous suspension, solution, elixir, and syrup.

14. The method according to claim 1, wherein the endometriosis-associated pain is selected from one or more of endometriosis-induced chronic pelvic pain, menstrual pain, pain with intercourse, low back pain, abdominal pain, vagina pain, and visceral organ pain.

15. The method according to claim 1, wherein the endometriosis-associated pain is endometriosis-induced painful bowel movements and/or painful urination during menstruation.

* * * * *